United States Patent
Mahmood et al.

(10) Patent No.: US 7,321,027 B2
(45) Date of Patent: Jan. 22, 2008

(54) SMALL TECHNETIUM-99M AND RHENIUM LABELED AGENTS AND METHODS FOR IMAGING TUMORS

(75) Inventors: Ashfaq Mahmood, Newton Center, MA (US); Matthias Friebe, Berlin (DE); Cristina Bolzati, Ferrara (IT); Alun G. Jones, Newton Center, MA (US); Alan Davison, North Falmouth, MA (US)

(73) Assignees: President and Fellows of Harvard College, Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/279,214

(22) Filed: Oct. 23, 2002

(65) Prior Publication Data

US 2004/0097735 A1   May 20, 2004

Related U.S. Application Data

(63) Continuation of application No. PCT/US01/13550, filed on Apr. 27, 2001.

(60) Provisional application No. 60/200,633, filed on Apr. 28, 2000.

(51) Int. Cl.
*C07F 13/00* (2006.01)
(52) U.S. Cl. .................. 534/14; 534/10; 534/15; 534/16; 424/1.11; 424/1.65
(58) Field of Classification Search .............. 424/1.11, 424/1.65, 9.1; 534/7, 10–16; 546/1; 514/183
See application file for complete search history.

(56) References Cited

U.S. PATENT DOCUMENTS 4,638,051 A   1/1987   Burns et al.
5,919,934 A   7/1999   John et al.

FOREIGN PATENT DOCUMENTS

EP   0 200 211   11/1986

OTHER PUBLICATIONS

P. Auzeloux et al. "A Potential Melanoma Tracer: Synthesis, Radiolabeling, and Biodistribution in Mice of a New Nitridotechnetium Bis (aminothiol) Derivative Pharmacomodulated by a N (Diethylaminoethyl) benzamide," J. Med. Chem. 2000, 43, 190-198.
John et al. "$^{99m}$Tc-Labeled σ-Receptor-Binding Complex: Synthesis, Characterization, and Specific Binding to Human Ductual Breast Carcinoma (T47D) Cells," Bioconjugate Chem. 8:304-309 (1997).

*Primary Examiner*—Dameron L. Jones
(74) *Attorney, Agent, or Firm*—Edwards Angell Palmer & Dodge LLP; George W. Neuner; Mark D. Russett

(57) ABSTRACT

The present invention relates to compounds and related technetium and rhenium complexes thereof which are suitable for imaging or therapeutic treatment of tumors, e.g., carcinomas, melanomas and other tumors. In another embodiment, the invention relates to methods of imaging tumors using radiolabeled metal complexes. Preferred radiolabeled complexes for imaging tumors include technetium and rhenium complexes. The high tumor uptake and significant tumor/nontumor ratios of the technetium complexes of the invention indicate that such small technetium-99m-based molecular probes can be developed as in-vivo diagnostic agents for melanoma and its metastases. In yet another embodiment, the invention relates to methods of treatment of tumors using a radiolabeled metal complex as a radiopharmaceutical agent to treat the tumor.

19 Claims, 13 Drawing Sheets

SMALL TECHNETIUM-99M AND RHENIUM LABELED AGENTS AND METHODS FOR IMAGING TUMORS

CROSS-REFERENCE TO RELATED APPLICATIONS

This application is a continuation of International Application PCT/US01/13550 filed on Apr. 27, 2001 and which designated the U.S.

The International application designated above, namely application PCT/US01/13550, filed Apr. 27, 2001, claims the benefit of U.S. Application No. 60/200,633 Apr. 28, 2000.

STATEMENT REGARDING FEDERALLY SPONSORED RESEARCH OR DEVELOPMENT

This invention was supported by National Institute of Health (NIH) Grant No. R01CA034870. The United States governement has certain rights to the invention.

FIELD OF THE INVENTION

The present invention relates to small molecular radiometal diagnostic agents for imaging tumors and radiometal therapeutic agents for treating same. More specifically, the present invention relates to small molecular technetium-99m diagnostic agents for imaging malignant melanoma and distant metastases and rhenium ($^{186}$Re, $^{188}$Re) therapeutic complexes for treating the same, $^{99m}$Tc-complexes and corresponding rhenium complexes having a disubstituted amino group linked through a nitrogen atom to the chelating ligand and, particularly where the amino group is substituted with lower alkyl groups.

BACKGROUND OF THE INVENTION

The increase in the incidence of skin cancer is of great concern. Nearly all deaths caused by skin malignancies result from malignant melanoma. The significant mortality of this disease is caused by the high proliferation rate of melanoma cells and the early occurrence of metastases. The choice of treatment depends on the timely detection of the melanoma and any associated metastases. Although positron emission tomography (PET) using 2-[$^{18}$F]fluoro-2-deoxy-D-glucose ($^{18}$F-FDG), an $^{18}$F-radiolabeled glucose analogue, has been successfully used for melanoma imaging, a $^{99m}$Tc-labeled single-photon-emission computed tomography (SPECT) radiopharmaceutical with affinity for melanoma may provide a cost effective and more widely available alternative for the same purpose.

Previous attempts to image melanoma with radiolabeled monoclonal antibodies have met with little success. Subsequent use of simpler radiolabeled molecules, including radioiodinated amino acids and nucleic acids as false precursors in the melanin formation cycle either displayed insufficient localization in tumors, and hence low tumor to nontumor ratios, or possessed poor pharmacokinetics. More promising results were recently obtained with $^{99m}$Tc-labeled α-melanotropin peptides. Tumor uptake and biodistribution studies with these radioconjugates generated favorable results, indicating that labeled peptides may be useful for in-vivo melanoma scintigraphy. The $^{99m}$Tc-complexes 1-4 have low melanoma uptake of 0.4% to 1.5% (% ID/g, 1 hour post injection) (Auzeloux, P., *J. Med. Chem.*, (2000) 43, pp. 190-199). Nevertheless, the search for non-peptidic, non-immunogenic, small molecules that possess high affinity for melanoma continues.

$^{99m}$Tc-complexes 1-4 and uptake thereof by melanoma cells.

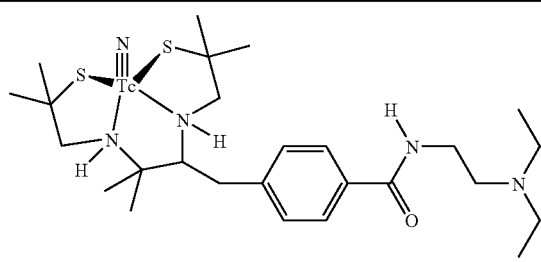

Compound 1
0.4% uptake

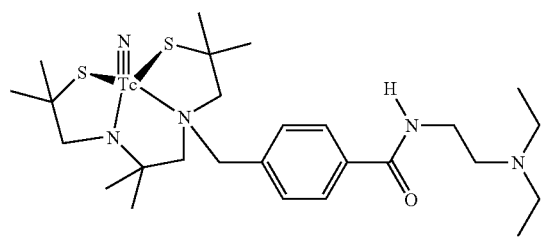

Compound 2
0.7% uptake

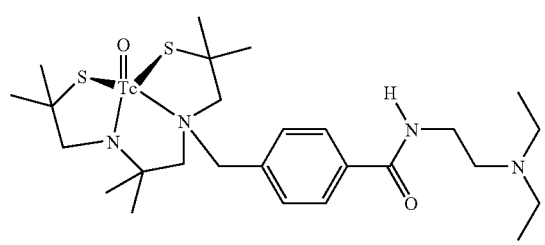

Compound 3
1.5% uptake

-continued

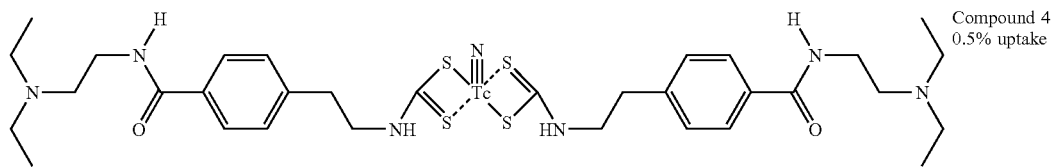

Compound 4
0.5% uptake

In this regard, melanoma uptake has been obtained with $^{123}$I-labeled N-(2-diethylaminoethyl)-4-iodobenzamide ([123I]BZA) and N-(2-diethylaminoethyl)-3-iodo-4-methoxybenzamide ([123I]IMBA). In-vivo investigations with these molecules in C57B16 mice transplanted subcutaneously with B16 melanoma cells showed uptake values ranging from 5% to 9% injected dose/g (ID/g) of tumor. Subsequent human clinical trials also indicated adequate uptake by melanoma and good scintigraphic images. Recent reports have suggested that the uptake is nonsaturable and may be related to the formation of melanin within the melanosome. Although such radioiodinated benzamides have entered phase II clinical trials for the diagnosis of malignant melanoma, their routine clinical use may be hampered by the associated disadvantages of iodine-123, i.e., in-vivo deiodination, lack of routine availability and high cost.

The most widely used isotope in clinical nuclear medicine, technetium-99m, possesses ideal characteristics ($t_{1/2}$= 6.02 h, 140 keV monoenergeric γ-emission) for nuclear medicine imaging and is available on demand from a $^{99}Mo$-$^{99m}Tc$ generator system. It is desirable to have a small technetium-99m labeled complex possessing high affinity for melanoma. Except for the $^{99m}Tc$-labeled α-melanotropin peptides, all of the tetradentate $^{99m}Tc$-complexes that have been published in literature in one form or the other rely on using the benzamides along with the aromatic ring in the overall structure of the complexes. Thus, new and useful $^{99m}Tc$-labeled diagnostic agents for melanoma imaging are still being sought.

SUMMARY OF THE INVENTION

The present invention provides new radiolabeled diagnostic and therapeutic agents which comprise a radiometal center. Preferred radiometals include 99m-technetium and one or more radioactive isotopes of rhenium. Preferred agents are useful for in-vivo and in-vitro imaging of tumors such as neoplasms, carcinoma and melanoma. Particularly preferred agents are useful for in-vivo and in-vitro imaging melanoma. Preferred agents of the present invention comprise an oxotechnetium core (Tc=O) or an oxorhenium core (Re=O) linked to a tertiary amine pharmacophore.

Thus, compounds of the invention comprise the following structure:

Y—X—NR$_1$R$_2$ where Y is a chelating ligand capable of binding technetium, X is a linking group containing a backbone chain having 1 to about 8 atoms, and R$_1$ and R$_2$ each are a lower alkyl group having 1 to about 4 carbon atoms, which can be the same or different and which can be substituted, and wherein NR$_1$R$_2$ taken in combination form a 3-8 member ring, which can include an additional hetero atom (from the combination of R$_1$ and R$_2$) such as an oxygen, sulfur or nitrogen atom. More preferably, the NR$_1$R$_2$ taken in combination form a 5, 6 or 7 member ring with 1 or 2 heteroatoms.

Preferred compounds of the invention capable of binding a metal ion include compounds according to formula I:

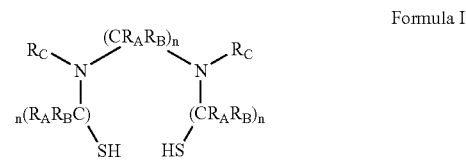

Formula I wherein:
R$_A$ is independently chosen at each occurrence of R$_A$ from the group consisting of hydrogen, lower alkyl having 1 to about 4 carbon atoms, alkyl ester groups having about 2 to about 8 carbon atoms, aryl ester groups having about 7 to about 18 carbon atoms, alkyl amide groups having about 2 to about 8 carbon atoms, aryl amide groups having about 7 to about 18 carbon atoms, di(alkyl)aminoalkyl groups where each alkyl group has 1 to about 4 carbon atoms, and —XNR$_1$R$_2$;

R$_B$ is hydrogen for each occurrence of R$_B$; or
—(CR$_A$R$_B$)— taken in combination is —C=O— such that there are zero or one —C=O— groups;

R$_C$ is independently selected at each occurrence of R$_C$ from the group consisting of hydrogen, lower alkyl groups having 1 to about 8 carbon atoms, alkyl ester or aryl ester groups having about 2 to about 8 carbon atoms, alkyl amide or aryl amide groups having about 2 to 8 carbon atoms, di(alkyl)aminoalkyl groups where each alkyl group has 1 to about 4 carbon atoms, and —XNR$_1$R$_2$;

X is a linking group comprising a backbone chain having 1 to about 8 atoms, the backbone chain can optionally include ester, amide, amine, ether or thioether linkages in the backbone chain and does not include aromatic groups integral to the backbone chain of the linking group; and R$_1$ and R$_2$ each are independently selected from a lower alkyl group having 1 to about 4 carbon atoms, or
—NR$_1$R$_2$ taken in combination is a heterocyclic ring having 3 to about 8 ring atoms and 1 or 2 hetero ring atoms;

n is either 2 or 3 and is independently chosen at each occurrence of n; and at least one occurrence of R$_A$ or R$_C$ in Formula I is chosen to be XNR$_1$R$_2$, where radiolabeled complex resulting from the binding of the compound to the metal ion is either neutral or cationic.

Preferred linking groups, X, are lower alkyl groups having from 1 to about 8 atoms in the backbone such as, e.g., —(CH$_2$)$_n$—, amine groups having 1 to 8 atoms in the backbone such as, e.g., —(CH$_2$)$_n$—NH(CH$_2$)$_m$—, ether groups having 1 to 8 atoms in the backbone such as, e.g., —(CH$_2$)$_n$—O—(CH$_2$)$_m$—, ester groups having 1 to 8 atoms in the backbone such as, e.g., —(CH$_2$)$_n$—CO—O—(CH$_2$)$_m$—, thioether groups having 1 to 8 atoms in the backbone such as, e.g., —(CH$_2$)$_n$—S—(CH$_2$)$_m$—, and amido groups having 5-8 atoms in the backbone such as, e.g., —(CH$_2$)$_n$CO—NH—CH$_2$CH$_2$— where n and m are non-negative integers and the sum n+m is typically between about 1 and about 8. Particularly preferred linking groups X have between about 2 and about 5 atoms in the backbone.

Preferred linking groups, X, of the invention have backbones which do not contain an aromatic group as an integral part of the backbone chain. Linking groups X may optionally have one or more substituents attached to the backbone chain including pendant aromatic groups. Preferred substituents include alkyl groups having from 1 to about 6 carbon atoms and from 0 to about 3 N, O or S atoms, hydroxyl, amino, carboxyl, alkoxy groups having from 1 to about 6 carbon atoms, aminoalkyl groups having from 1 to about 6 carbon atoms, dialkylaminoalkyl groups where each alkyl group has from about 1 to about 6 carbon atoms, halogen atoms including F, Cl, Br, and I, aromatic groups having about 5 to about 18 ring atoms which may include 0, 1, 2, or 3 N, O or S ring atoms.

The compounds of the invention are then complexed with a radiometal ion using methods well known in the art to provide radiolabeled complexes. Typical radiolabeled complexes of the invention are cationic or neutral. Preferred radiometal ions include isotopes of metal ions that emit α, β, or γ radiation, including metal ions selected from the group consisiting of technetium, rhenium, yttrium, copper, gallium, indium, bismuth, platinum and rhodium. Particularly preferred radiolabeled complexes of the invention comprise a technetium or rhenium metal ion.

The present invention also provides methods for in-vivo or in-vitro imaging of at least one tumor comprising the steps of:

providing a radiolabeled complex comprising a metal ion and a compound of the following structure:

Y—X—NR$_1$R$_2$ wherein

Y is a chelating ligand capable of binding the metal ion;

X is a linking group comprising a backbone chain having 1 to about 8 atoms, the backbone chain can optionally include ester, amide, amine, ether or thioether linkages in the backbone chain and does not include aromatic groups integral to the backbone chain of the linking group; and R$_1$ and R$_2$ each are independently selected from a lower alkyl group having 1 to about 4 carbon atoms, or —NR$_1$R$_2$ taken in combination is a heterocyclic ring having 3 to about 8 ring atoms and 1 or 2 hetero ring atoms;

contacting the tumor(s) with the radiolabeled complex; and making a radiographic image to image the tumor(s).

In preferred embodiments, the radiolabeled complexes are injected into a mammal to obtain an image of at least one tumor such as a neoplasm, carcinoma or melanoma. Preferable radiolabeled complexes accumulate in tumor. Images are obtained by conventional techniques such as use of a radioscintillation camera.

DEFINITIONS

Figure 1:
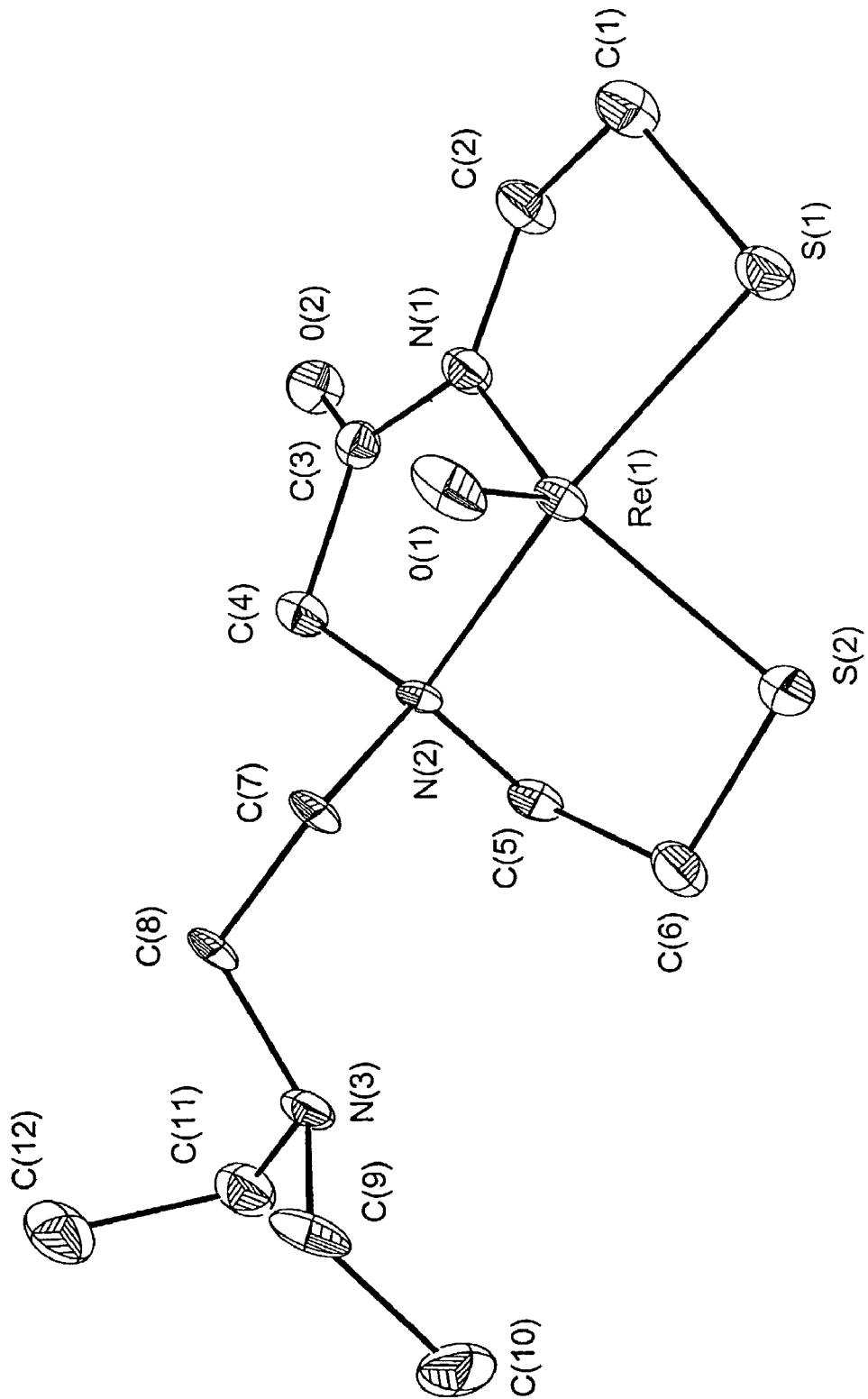
FIG. 1 is an illustration of the solid state structure of a rhenium complex of the invention (Re-Compound A)
Figure 2:
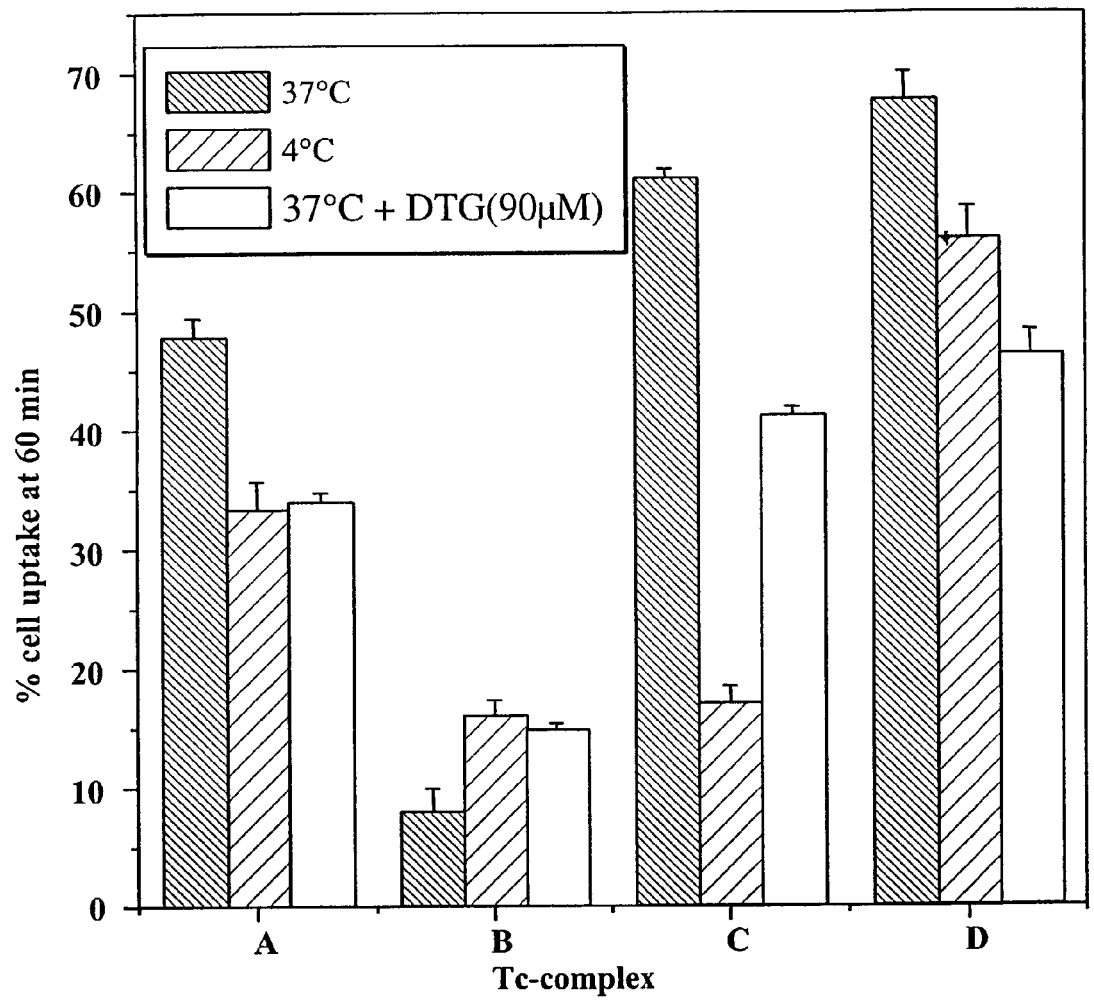
FIG. 2 is a graph illustrating the in-vitro uptake of $^{99m}$Tc-labeled complex of Compounds A-D of the present invention in melanoma cells at different temperatures.
Figure 3:
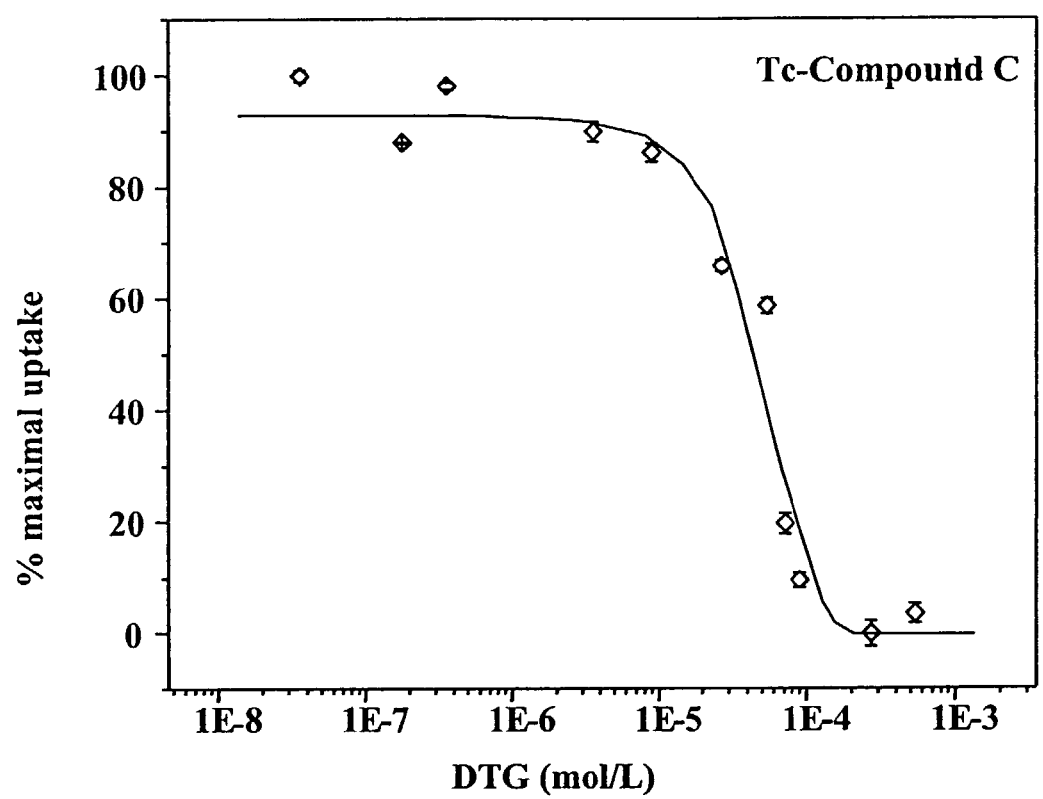
FIG. 3 is a graph illustrating the maximal uptake of $^{99m}$Tc-labeled complex of Compound C of the present invention in melanoma cells at different concentrations of DTG.

Tr and Trt refer to trityl groups, e.g., triphenylmethyl groups. DTG refers to ditolyl guanidine.

AADT refers to amino-amido-dithiolate ligands, preferred AADT ligands have a N-[2-(2-mercapto-ethylamino)-ethylamino]-ethanethiol structure.

DADT refers to diamino-dithiolate ligands, preferred DADT ligands have a 2-[2-(2-mercapto-ethylamino)-ethylamino]-ethanethiol structure.

DETAILED DESCRIPTION OF THE INVENTION AND PREFERRED EMBODIMENTS THEREOF

The present invention provides new radiolabeled diagnostic and therapeutic agents which comprise a radiometal center. Preferred radiometals include 99m-technetium and one or more radioactive isotopes of rhenium. Preferred agents are useful for in-vivo and in-vitro imaging of tumors such as neoplasms, carcinoma and melanoma. Particularly preferred agents are useful for in-vivo and in-vitro imaging melanoma. Preferred agents of the present invention typically comprise an oxotechnetium core (Tc═O) or an oxorhenium core (Re═O) chelated by at least one ligand group Y linked to a tertiary amine pharmacophore. Preferred radiolabeled metal complexes of the invention comprise a neutral or cationic metal complex, e.g., a metal ion and the inner coordination sphere of ligands taken together are neutral or cationic. Preferably, the overall charge of the radiolabeled complex is also neutral or cationic.

Thus, compounds of the invention comprise the following structure:

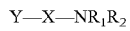

where Y is a chelating ligand capable of binding technetium, X is a linking group containing a backbone chain having 1 to about 8 atoms, and $R_1$ and $R_2$ are independently chosen lower alkyl groups, each lower alkyl group having 1 to about 4 carbon atoms, can be the same or different and can be substituted, and wherein $NR_1R_2$ taken in combination a 3-8 member ring, which can include an additional hetero atom. Preferred heterocyclic rings have 5, 6, or 7 ring atoms and comprise 1 or 2 heteroatoms. Particularly preferred heterocyclic rings are morpholino, piperidinyl, piperizinyl and thiomorpholino.

Radiolabeled complexes of the present invention can be isomerically pure or can comprise a mixture of isomers including mixtures of two or more isomers selected from enantiomers, diastereomers, complexation isomers, rotational isomers, geometric isomers, tautomers and like isomers. For example, isomeric complexes which result from the relative orientation of metal ligand group and a substitutents on the metal chelate group, Y, such as $R_A$ or $R_C$ or $XNR_1R_2$ are typically referred to as syn/anti isomers or alternatively as cis/trans isomers where the syn isomer has the oxo ligand and the ligand substituent oriented in generally the same direction and the anti isomer has the oxo ligand and the ligand substituent oriented in generally opposite directions.

Preferred metal ions for use in radiolabeled complexes of the invention are sources of capable of emiting one or more discrete forms of radiation. Preferred radiation emissions include alpha, beta and gamma radiation emissions. Additionally preferred are metal ions that emit alpha, beta or gamma radiation with sufficient energy to be detected by standard radiography techniques or have sufficient alpha, beta or gamma energy for radiotherapeutic applications. Particularly preferred metal ions include one or more isotopes of metals selected from technetium, rhenium, ytttium, copper, gallium, indium, bismuth, platinum and rhodium. Technetium-99m and radioactive isotopes of rhenium are exemplary metal ion for use in the present invention. Metal ions suitable for use in radiolabeled complexes of the invention may include additional ligands coordinated to the metal atom. Preferred ligands include oxo, nitride, fluoride, chloride, bromide, iodide, carbonyl, isonitrile, nitrile, nitrosyl, alkoxide groups with 1 to about 6 carbon atoms, amine groups with 1 to about 12 carbon atoms, water, ether groups with 2 to about 8 carbon atoms, thioether groups with 2 to about 8 carbon atoms including thiophene, phosphines and phosphates with 1 to about 20 carbon atoms and other common ligands for technetium and rhenium chemistry. Particularly preferred technetium and rhenium metal ions additionally comprise an oxo ligand, e.g., a Tc=O or Re=O.

Additionally, preferred complexes of the invention have a chelating ligand moiety, Y, where the chelating ligand is able to bind to a metal ion through a plurality of donor atoms. Each donor atom is typically C, N, O, S, or P but other donor atoms are also acceptable for certain applications. Preferred donor atoms are N and S. The plurality of donor atoms can be present in a single compound or can be present in two or more compounds such that the two compounds bind to the metal to form the chelating ligand-metal complex. In certain embodiments, one compound will comprise three donor atoms and one or more additional compound will each independently comprise a single donor atom. Alternatively, two compounds, which can be the same or different, each of which can independently comprise two or more donor atoms can bind to a metal center to form a bis-ligand metal complex.

Particularly preferred compounds and radiolabeled metal complexes comprise a tetradentate ligand system wherein the tetradentate ligand is contained in a single compound that includes four donor atoms. In additional preferred compounds and radiolabeled metal complexes, the tetradentate chelating ligand is a "3+1" ligand system wherein three donor atoms of the tetradentate chelating ligand moiety Y are contained in one compound and the fourth donor atom is present in another compound.

Preferred linking groups, X, are lower alkyl groups having from 1 to about 8 atoms in the backbone such as, e.g., —$(CH_2)_n$—, amine groups having 3 to 8 atoms in the backbone such as, e.g., —$(CH_2)_n$—NH—$(CH_2)_m$—, ether groups having 3 to 8 atoms in the backbone such as, e.g., —$(CH_2)_n$—O—$(CH_2)_m$—, ester groups having 4 to 8 atoms in the backbone such as, e.g., —$(CH_2)_n$—CO—O—$(CH_2)_m$—, thioether groups having 3 to 8 atoms in the backbone such as, e.g., —$(CH_2)_n$—S—$(CH_2)_m$—, and amido groups having 4-8 atoms in the backbone such as, e.g., —$(CH_2)_n$CO—NH—$(CH_2)_m$— where n and m are non-negative integers and the sum n+m is typically between about 2 and about 8. Particularly preferred linking groups X have between about 2 and about 5 atoms in the backbone.

Preferred linking groups, X, of the invention have backbones which do not contain an aromatic group as an integral part of the backbone chain. Linking groups X may optionally have one or more substituents attached to the backbone chain including pendant aromatic groups. Preferred substituents include alkyl groups having from 1 to about 6 carbon atoms and from 0 to about 3 N, O or S atoms, hydroxyl, amino, carboxyl, alkoxy groups having from 1 to about 6 carbon atoms, aminoalkyl groups having from 1 to about 6 carbon atoms, dialkylaminoalkyl groups where each alkyl group has from about 1 to about 6 carbon atoms, halogen atoms including F, Cl, Br, and I, aromatic groups having about 5 to about 18 ring atoms which may include 0, 1, 2, or 3 N, O or S ring atoms.

Preferred $NR_1R_2$ include groups where $R_1$ and $R_2$ each are independently selected alkyl groups having about 1 to about 6 carbon atoms. More preferred are groups where $R_1$ and $R_2$ are alkyl groups having about 2 to about 4 carbon atoms such as ethyl, n-propyl and n-butyl. Alternatively, preferred compounds include compounds wherein the $NR_1R_2$ group is taken in combination to form a heterocyclic ring. Preferably the heterocyclic ring has between 3 and about 8 ring atoms and the ring can optionally contain 0, 1 or 2 additional N, O or S atoms. More preferred are 5, 6 and 7 membered heterocyclic rings. Exemplary heterocyclic rings include N-piperidinyl, N-piperizinyl, N-morpholinyl, and N-thiomorpholinyl.

Examples of preferred X—$NR_1R_2$ groups of ligands, Y—X—$NR_1R_2$, of the present invention include:

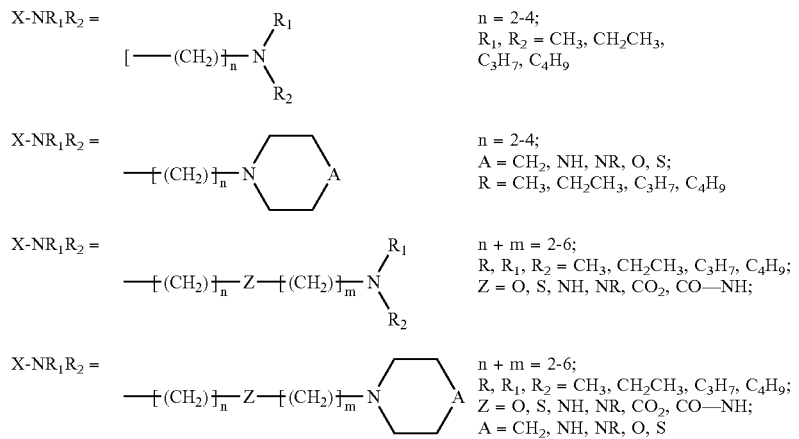

| X-NR₁R₂ = | | |
|---|---|---|
| | [—(CH₂)]ₙ—N(R₁)(R₂) | n = 2-4; R₁, R₂ = CH₃, CH₂CH₃, C₃H₇, C₄H₉ |
| X-NR₁R₂ = | —[(CH₂)]ₙ—N⟨ring⟩A | n = 2-4; A = CH₂, NH, NR, O, S; R = CH₃, CH₂CH₃, C₃H₇, C₄H₉ |
| X-NR₁R₂ = | —[(CH₂)]ₙ—Z—[(CH₂)]ₘ—N(R₁)(R₂) | n + m = 2-6; R, R₁, R₂ = CH₃, CH₂CH₃, C₃H₇, C₄H₉; Z = O, S, NH, NR, CO₂, CO—NH; |
| X-NR₁R₂ = | —[(CH₂)]ₙ—Z—[(CH₂)]ₘ—N⟨ring⟩A | n + m = 2-6; R, R₁, R₂ = CH₃, CH₂CH₃, C₃H₇, C₄H₉; Z = O, S, NH, NR, CO₂, CO—NH; A = CH₂, NH, NR, O, S |

Radiolabeled complexes of the invention include neutral or cationic metal centers where the metal center refers to the metal ion and the inner sphere of ligands directly bound to the metal ion. Preferred radiolabeled complexes of the invention contain a metal center that is neutral or cationic. Moreover, the radiolabeled complex comprising a metal ion and a compound of the formula Y—X—NR₁R₂ taken in its entirety is neutral or cationic.

The invention provides compounds capable of binding a metal ion, the compounds are of Formula I:

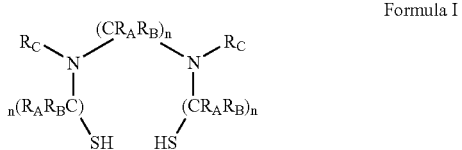

Formula I wherein:

$R_A$ is independently chosen at each occurrence of $R_A$ from the group consisting of hydrogen, lower alkyl having 1 to about 4 carbon atoms, alkyl ester groups having about 2 to about 8 carbon atoms, aryl ester groups having about 7 to about 18 carbon atoms, alkyl amide groups having about 2 to about 8 carbon atoms, aryl amide groups having about 7 to about 18 carbon atoms, di(alkyl)aminoalkyl groups where each alkyl group has 1 to about 4 carbon atoms, and —XNR₁R₂;

$R_B$ is hydrogen for each occurrence of $R_B$; or —(CR_AR_B)— taken in combination is —C=O— such that there are zero or one —C=O— groups;

$R_C$ is independently selected at each occurrence of $R_C$ from the group consisting of hydrogen, lower alkyl groups having 1 to about 8 carbon atoms, alkyl ester or aryl ester groups having about 2 to about 8 carbon atoms, alkyl amide or aryl amide groups having about 2 to 8 carbon atoms, di(alkyl)aminoalkyl groups where each alkyl group has 1 to about 4 carbon atoms, and —XNR₁R₂;

X is a linking group comprising a backbone chain having 1 to about 8 atoms, the backbone chain can optionally include ester, amide, amine, ether or thioether linkages in the backbone chain and does not include aromatic groups integral to the backbone chain of the linking group; and $R_1$ and $R_2$ each are independently selected from a lower alkyl group having 1 to about 4 carbon atoms, or —NR₁R₂ taken in combination is a heterocyclic ring having 3 to about 8 ring atoms and 1 or 2 hetero ring atoms; and n is either 2 or 3 and is independently chosen at each occurrence of n, at least one occurrence of $R_A$ or $R_C$ in Formula I is chosen to be XNR₁R₂, where the radiolabeled complex resulting from the binding of the compound to the metal ion is either neutral or cationic.

Preferred compounds of Formula I are capable of binding a metal ion selected from the group consisting of technetium, rhenium, yttrium, copper, gallium, indium, bismuth, platinum and rhodium. Particularly preferred compounds are capable of binding technetium-99m or an isotope of rhenium.

Additionally preferred compounds of Formula I have NR₁R₂ taken in combination to form a carbocyclic or heterocyclic ring wherein the ring has 3 to about 7 ring atoms. Preferred heterocyclic rings have at least one nitrogen, oxygen or sulfur atom. Exemplary examples of heterocyclic rings include N-morpholino, N-piperidinyl, N-piperazinyl or thiomorpholino.

Still other preferred compounds of Formula I are compounds having X is —(CH₂)_q—, —(CH₂)_m C(O)NH—(CH₂)_p—, or —(CH₂)_m C(O)O—(CH₂)_p—;

m and p are independently chosen at each occurrence of m and p to be 1 to about 3; and q is independently chosen at each occurrence of q to be a number from 1 to about 6.

Other preferred compounds of Formula I are compounds wherein:

$R_1$ and $R_2$ each are independently selected from lower alkyl group having 1 to about 4 carbon atoms; or —NR₁R₂ taken in combination is a heterocyclic ring according to the formula:

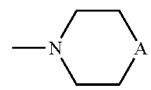

where A is CH₂, NR_D, O or S;

$R_D$ is chosen from the group consisting of hydrogen, lower alkyl group having from 1 to about 4 carbon atoms, aralkyl groups having from 7 to about 18 carbon atoms, aryl groups having 6 to about 18 carbon atoms, alkyl ester groups having about 2 to about 8 carbon atoms, aryl ester groups having about 7 to about 18 carbon atoms, alkyl amide groups having about 2 to about 8 carbon atoms, aryl amide groups having about 7 to about 18 carbon atoms, di(alkyl)aminoalkyl groups where each alkyl group has 1 to about 4 carbon atoms, —XNR₁R₂.

Additional useful compounds of Formula I include compounds according to Formula II.

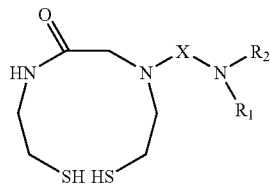

Formula II wherein:

R₁ and R₂ each are independently selected from lower alkyl group having 1 to about 4 carbon atoms; or —NR₁R₂ taken in combination is a heterocyclic ring according to the formula:

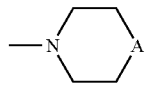

where A is $CH_2$, $NR_D$, O or S;

$R_D$ is chosen from the group consisting of hydrogen, lower alkyl group having from 1 to about 4 carbon atoms, aralkyl groups having from 7 to about 18 carbon atoms, aryl groups having 6 to about 18 carbon atoms, alkyl ester groups having about 2 to about 8 carbon atoms, aryl ester groups having about 7 to about 18 carbon atoms, alkyl amide groups having about 2 to about 8 carbon atoms, aryl amide groups having about 7 to about 18 carbon atoms, di(alkyl)aminoalkyl groups where each alkyl group has 1 to about 4 carbon atoms, —XNR₁R₂;

X is —$(CH_2)_q$—, —$(CH_2)_mC(O)NH$—$(CH_2)_p$—, or —$(CH_2)_mC(O)O$—$(CH_2)_p$—;

m and p are independently chosen at each occurrence of m and p to be 1 to about 3; and q is independently chosen at each occurrence of q to be a number from 1 to about 6.

Additional useful compounds of Formula I include compounds according to Formula III.

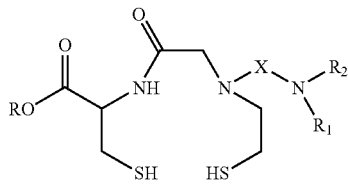

Formula III wherein:

R is lower alkyl group having 1 to about 8 carbon atoms, alkoxyalkyl groups having 2 to about 8 carbon atoms, or aralkyl groups having 6 to about 2 carbon atoms;

R₁ and R₂ each are independently selected from lower alkyl group having 1 to about 4 carbon atoms; or —NR₁R₂ taken in combination is a heterocyclic ring according to the formula:

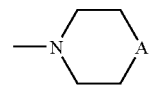

where A is $CH_2$, $NR_D$, O or S;

$R_D$ is chosen from the group consisting of hydrogen, lower alkyl group having from 1 to about 4 carbon atoms, aralkyl groups having from 7 to about 18 carbon atoms, aryl groups having 6 to about 18 carbon atoms, alkyl ester groups having about 2 to about 8 carbon atoms, aryl ester groups having about 7 to about 18 carbon atoms, alkyl amide groups having about 2 to about 8 carbon atoms, aryl amide groups having about 7 to about 18 carbon atoms, di(alkyl)aminoalkyl groups where each alkyl group has 1 to about 4 carbon atoms, —XNR₁R₂;

X is —$(CH_2)_q$—, —$(CH_2)_mC(O)NH$—$(CH_2)_p$—, or —$(CH_2)_mC(O)O$—$(CH_2)_p$—;

m and p are independently chosen at each occurrence of m and p to be 1 to about 3; and q is independently chosen at each occurrence of q to be a number from 1 to about 6.

Additional useful compounds of Formula I include compounds according to Formula IV.

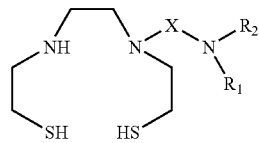

Formula IV wherein:

R₁ and R₂ each are independently selected from lower alkyl group having 1 to about 4 carbon atoms; or —NR₁R₂ taken in combination is a heterocyclic ring according to the formula:

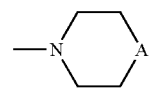

where A is $CH_2$, $NR_D$, O or S;

$R_D$ is chosen from the group consisting of hydrogen, lower alkyl group having from 1 to about 4 carbon atoms, aralkyl groups having from 7 to about 18 carbon atoms, aryl groups having 6 to about 18 carbon atoms, alkyl ester groups having about 2 to about 8 carbon atoms, aryl ester groups having about 7 to about 18 carbon atoms, alkyl amide groups having about 2 to about 8 carbon atoms, aryl amide groups having about 7 to about 18 carbon atoms, di(alkyl)aminoalkyl groups where each alkyl group has 1 to about 4 carbon atoms, —XNR₁R₂;

X is —$(CH_2)_q$—, —$(CH_2)_mC(O)NH$—$(CH_2)_p$—, or —$(CH_2)_mC(O)O$—$(CH_2)_p$—;

m and p are independently chosen at each occurrence of m and p to be 1 to about 3; and q is independently chosen at each occurrence of q to be a number from 1 to about 6.

In another embodiment, the present invention provides radiolabeled complexes wherein the metal complex is neutral or cationic that include a compound according to Formula I and a metal ion. Additional preferred radiolabeled complexes comprise a metal ion and a compound of any of Formulas II, III, IV. Preferred metal ions for use in radiolabeled complexes of the invention are sources of capable of emitting one or more discrete forms of radiation. Preferred radiation emissions include alpha, beta and gamma radiation emissions. Additionally preferred are metal ions that emit alpha, beta or gamma radiation with sufficient energy to be detected by standard radiography techniques or have sufficient alpha, beta or gamma energy for radiotherapeutic applications. Particularly preferred metal ions include one or more isotopes of metals selected from technetium, rhenium, ytttium, copper, gallium, indium, bismuth, platinum and rhodium. Technetium-99m and radioactive isotopes of rhenium are exemplary metal ion for use in the present invention.

Other ligands may also be present in metal ions in certain embodiments of the invention. Preferred ligands include oxo, nitride, fluoride, chloride, bromide, iodide, carbonyl, isonitrile, nitrile, nitrosyl, alkoxide groups with 1 to about 6 carbon atoms, amine groups with 1 to about 12 carbon atoms, water, ether groups with 2 to about 8 carbon atoms, thioether groups including thiophene with 2 to about 8 carbon atoms and 1, 2, or 3 nitrogen atoms, phosphines with 1 to about 20 carbon atoms and other common ligands for technetium and rhenium chemistry. Preferred technetium and rhenium metal ions additionally comprise an oxo ligand, e.g., a Tc=O or Re=O.

Particularly preferred radiolabeled complexes of the invention include complexes according to Formula V, VI, or VII:

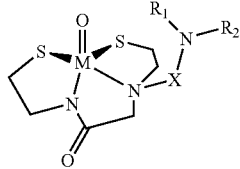

Formula V

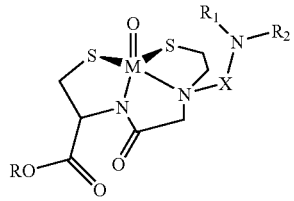

Formula VI

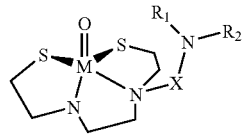

Formula VII wherein the variables present in Formula V, VI and VII have the definitions:

M is at least one isotope of technetium or rhenium;

R is lower alkyl group having 1 to about 8 carbon atoms, alkoxyalkyl groups having 2 to about 8 carbon atoms, or aralkyl groups having 6 to about 2 carbon atoms;

$R_1$ and $R_2$ each are independently selected from a lower alkyl group having 1 to about 4 carbon atoms; or —$NR_1R_2$ taken in combination is a heterocyclic ring according to the formula:

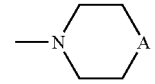

where A is $CH_2$, $NR_D$, O or S;

$R_D$ is chosen from the group consisting of hydrogen, lower alkyl group having from 1 to about 4 carbon atoms, aralkyl groups having from 7 to about 18 carbon atoms, aryl groups having 6 to about 18 carbon atoms, alkyl ester groups having about 2 to about 8 carbon atoms, aryl ester groups having about 7 to about 18 carbon atoms, alkyl amide groups having about 2 to about 8 carbon atoms, aryl amide groups having about 7 to about 18 carbon atoms, di(alkyl)aminoalkyl groups where each alkyl group has 1 to about 4 carbon atoms, —$XNR_1R_2$;

X is —$(CH_2)_q$—, —$(CH_2)_mC(O)NH$—$(CH_2)_p$—, or —$(CH_2)_mC(O)O$—$(CH_2)_p$—;

m and p are independently chosen at each occurrence of m and p to be 1 to about 3; and q is independently chosen at each occurrence of q to be a number from 1 to about 6.

The invention also provides a method for the in-vivo or in-vitro imaging of at least one tumor. The method comprises the steps of:

providing a radiolabeled complex comprising a metal ion and a compound of the following structure:

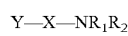

Y—X—$NR_1R_2$ wherein

Y is a chelating ligand capable of binding the metal ion;

X is a linking group comprising a backbone chain having 1 to about 8 atoms, the backbone chain can optionally include ester, amide, amine, ether or thioether linkages in the backbone chain and does not include aromatic groups integral to the backbone chain of the linking group; and $R_1$ and $R_2$ each are independently selected from a lower alkyl group having 1 to about 4 carbon atoms, or —$NR_1R_2$ taken in combination is a heterocyclic ring having 3 to about 8 ring atoms and 1 or 2 hetero ring atoms; and contacting the tumor(s) with the radiolabeled complex; and making a radiographic image to image the tumor(s).

Preferred metal ions for use in the method of imaging tumors include radioisotopes of technetium, rhenium, yttrium, copper, gallium, indium, bismuth, platinum and rhodium. Particularly preferred metal ions include technetium-99m or one or more isotopes of rhenium.

Other ligands may also be present in metal ions in certain embodiments of the invention. Preferred ligands include oxo, nitride, fluoride, chloride, bromide, iodide, carbonyl, isonitrile, nitrile, nitrosyl, alkoxide groups with 1 to about 6 carbon atoms, amine groups with 1 to about 12 carbon atoms, water, ether groups with 2 to about 8 carbon atoms, thioether groups including thiophene with 2 to about 8 carbon atoms and 1, 2, or 3 nitrogen atoms, phosphines with 1 to about 20 carbon atoms and other common ligands for technetium and rhenium chemistry. Preferred technetium and rhenium metal ions additionally comprise an oxo ligand, e.g., a Tc=O or Re=O.

Tumors suitable for imaging by the method of the present invention include neoplasms, carcinomas and other cancerous tumors. Preferred tumors for imaging include neoplasms of breast, prostate, lung, pancreas, liver, colon, lymphomas, gliomas and other neoplasms. Particularly preferred tumors for imaging include melanomas such as malignant melanomas, metathesized melanomas and melanoma tumors distant from the original melanoma tumor site. Tumors, especially neoplasm and melanoma tumors, can be imaged in-vivo or in-vitro in any tissue. Preferably the tumor to be imaged is in a mammalian tissue, more preferably the tumor is in a human tissue. Preferred tissues and organs include skin, heart, brain, lung, spleen, colon, liver, kidney, muscle, and other internal organs.

In preferred methods of the invention, the radiolabeled complex comprises a compound of the formula:

Y—X—NR$_1$R$_2$ wherein Y is a chelating ligand capable of binding a metal ion selected from the group consisting of technetium, rhenium, yttrium, copper, gallium, indium, bismuth, platinum and rhodium. Particularly preferred compounds have Y being a tetradentate chelating ligand capable of binding technetium-99m and/or one or more isotopes of rhenium.

Particularly preferred ligands include Y being an amido-amino-dithiolate group or a diamino-dithiolate group where the nitrogen and sulfur atoms capable of binding technetium are linked by ethylene or propylene groups wherein each carbon of the ethylene or propylene linker groups are substituted with one or more substituents chosen from the group consisting of hydrogen, lower alkyl having 1 to about 4 carbon atoms, alkyl ester groups having about 2 to about 8 carbon atoms, aryl ester groups having about 7 to about 18 carbon atoms, alkyl amide groups having about 2 to about 8 carbon atoms, aryl amide groups having about 7 to about 18 carbon atoms, oxo, and —XNR$_1$R$_2$ as defined in Formula I.

Additionally preferred methods include the use of compounds wherein the NR$_1$R$_2$ group taken in combination is a heterocyclic ring according to the formula:

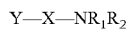

where A is CH$_2$, NR$_D$, O or S;

R$_D$ is chosen from the group consisting of hydrogen, lower alkyl group having from 1 to about 4 carbon atoms, aralkyl groups having from 7 to about 18 carbon atoms, aryl groups having 6 to about 18 carbon atoms, alkyl ester groups having about 2 to about 8 carbon atoms, aryl ester groups having about 7 to about 18 carbon atoms, alkyl amide groups having about 2 to about 8 carbon atoms, aryl amide groups having about 7 to about 18 carbon atoms, di(alkyl)aminoalkyl groups where each alkyl group has 1 to about 4 carbon atoms, —XNR$_1$R$_2$.

Particularly preferred methods include complexes comprising a metal ion and a compound according to Formula I:

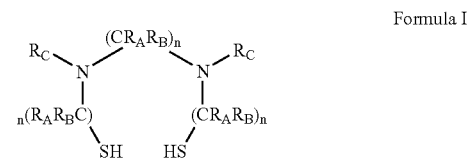

wherein

R$_A$ and R$_B$ are independently chosen at each occurrence of R$_A$ and R$_B$ in the ligand from the group consisting of hydrogen, lower alkyl having 1 to about 4 carbon atoms, alkyl ester groups having about 2 to about 8 carbon atoms, aryl ester groups having about 7 to about 18 carbon atoms, alkyl amide groups having about 2 to about 8 carbon atoms, aryl amide groups having about 7 to about 18 carbon atoms, di(alkyl)aminoalkyl groups where each alkyl group has 1 to about 4 carbon atoms, and —XNR$_1$R$_2$; or —(CR$_A$R$_B$)— taken in combination is —C=O—;

R$_C$ is independently selected at each occurrence of R$_C$ from the group consisting of hydrogen, lower alkyl groups having 1 to about 8 carbon atoms, alkyl ester groups having about 2 to about 8 carbon atoms, aryl ester groups having about 7 to about 18 carbon atoms, alkyl amide groups having about 2 to about 8 carbon atoms, aryl amide groups having about 7 to about 18 carbon atoms, di(alkyl)aminoalkyl groups where each alkyl group has 1 to about 4 carbon atoms, and —XNR$_1$R$_2$;

X is a linking group comprising a backbone chain having 1 to about 8 atoms, the backbone chain can optionally include ester, amide, amine, ether or thioether linkages in the backbone chain and does not include aromatic groups integral to the backbone chain of the linking group; and R$_1$ and R$_2$ each are independently selected from a lower alkyl group having 1 to about 4 carbon atoms, or —NR$_1$R$_2$ taken in combination is a heterocyclic ring having 3 to about 8 ring atoms and 1 or 2 hetero ring atoms;

n is either 2 or 3 and is independently chosen at each occurrence of n; and at least one occurrence of R$_A$ or R$_C$ in Formula I is chosen to be XNR$_1$, R$_2$, where the radiolabeled complex resulting from the binding of the compound to the metal ion is either neutral or cationic.

Still other preferred compounds of Formula I for use in methods for imaging tumors of the present invention are compounds having X is —CH$_2$)$_q$—, —(CH$_2$)$_m$C(O)NH—(CH$_2$)$_p$—, or —(CH$_2$)$_n$C(O)O—(CH$_2$)$_p$—;

m and p are independently chosen at each occurrence of m and p to be 1 to about 3; and q is independently chosen at each occurrence of q to be a number from 1 to about 6.

Other preferred compounds of Formula I for use in methods for imaging tumors of the present invention are compounds wherein:

R$_1$ and R$_2$ each are independently selected from lower alkyl group having 1 to about 4 carbon atoms; or —NR$_1$R$_2$ taken in combination is a heterocyclic ring according to the formula:

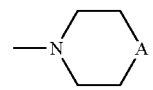

where A is CH$_2$, NR$_D$, O or S;

$R_D$ is chosen from the group consisting of hydrogen, lower alkyl group having from 1 to about 4 carbon atoms, aralkyl groups having from 7 to about 18 carbon atoms, aryl groups having 6 to about 18 carbon atoms, alkyl ester groups having about 2 to about 8 carbon atoms, aryl ester groups having about 7 to about 18 carbon atoms, alkyl amide groups having about 2 to about 8 carbon atoms, aryl amide groups having about 7 to about 18 carbon atoms, di(alkyl)aminoalkyl groups where each alkyl group has 1 to about 4 carbon atoms, —$XNR_1R_2$.

In another preferred method of the invention include radiolabeled complexes that comprise a metal ion and a compound is of Formula II:

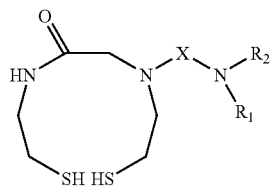

Formula II wherein:

$R_1$ and $R_2$ each are independently selected from lower alkyl group having 1 to about 4 carbon atoms; or —$NR_1R_2$ taken in combination is a heterocyclic ring according to the formula:

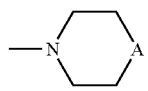

where A is $CH_2$, $NR_D$, O or S;

$R_D$ is chosen from the group consisting of hydrogen, lower alkyl group having from 1 to about 4 carbon atoms, aralkyl groups having from 7 to about 18 carbon atoms, aryl groups having 6 to about 18 carbon atoms, alkyl ester groups having about 2 to about 8 carbon atoms, aryl ester groups having about 7 to about 18 carbon atoms, alkyl amide groups having about 2 to about 8 carbon atoms, aryl amide groups having about 7 to about 18 carbon atoms, di(alkyl)aminoalkyl groups where each alkyl group has 1 to about 4 carbon atoms, —$XNR_1R_2$;

X is —$(CH_2)_q$—, —$(CH_2)_mC(O)NH$—$(CH_2)_p$—, or —$(CH_2)_mC(O)O$—$(CH_2)_p$—;

m and p are independently chosen at each occurrence of m and p to be 1 to about 3; and q is independently chosen at each occurrence of q to be a number from 1 to about 6.

In another preferred method of the invention include radiolabeled complexes that comprise a metal ion and a compound is of Formula III.

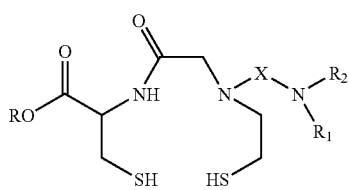

Formula III wherein:

R is lower alkyl group having 1 to about 8 carbon atoms, alkoxyalkyl groups having 2 to about 8 carbon atoms, or aralkyl groups having 6 to about 2 carbon atoms;

$R_1$ and $R_2$ each are independently selected from lower alkyl group having 1 to about 4 carbon atoms; or t —$NR_1R_2$ taken in combination is a heterocyclic ring according to the formula:

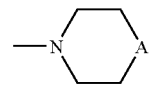

where A is $CH_2$, $NR_D$, O or S;

$R_D$ is chosen from the group consisting of hydrogen, lower alkyl group having from 1 to about 4 carbon atoms, aralkyl groups having from 7 to about 18 carbon atoms, aryl groups having 6 to about 18 carbon atoms, alkyl ester groups having about 2 to about 8 carbon atoms, aryl ester groups having about 7 to about 18 carbon atoms, alkyl amide groups having about 2 to about 8 carbon atoms, aryl amide groups having about 7 to about 18 carbon atoms, di(alkyl)aminoalkyl groups where each alkyl group has 1 to about 4 carbon atoms, —$XNR_1R_2$;

X is —$(CH_2)_q$—, —$(CH_2)_mC(O)NH$—$(CH_2)_p$—, or —$(CH_2)_mC(O)O$—$(CH_2)_p$—;

m and p are independently chosen at each occurrence of m and p to be 1 to about 3; and q is independently chosen at each occurrence of q to be a number from 1 to about 6.

In another preferred method of the invention include radiolabeled complexes that comprise metal ion and a compound is of Formula IV.

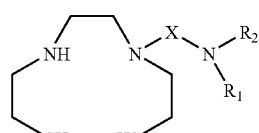

Formula IV wherein:

$R_1$ and $R_2$ each are independently selected from lower alkyl group having 1 to about 4 carbon atoms; or —$NR_1R_2$ taken in combination is a heterocyclic ring according to the formula:

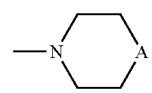

where A is $CH_2$, $NR_D$, O or S;

$R_D$ is chosen from the group consisting of hydrogen, lower alkyl group having from 1 to about 4 carbon atoms, aralkyl groups having from 7 to about 18 carbon atoms, aryl groups having 6 to about 18 carbon atoms, alkyl ester groups having about 2 to about 8 carbon atoms, aryl ester groups having about 7 to about 18 carbon atoms, alkyl amide groups having about 2 to about 8 carbon atoms, aryl amide groups having about 7 to about 18 carbon atoms, di(alkyl)aminoalkyl groups where each alkyl group has 1 to about 4 carbon atoms, —$XNR_1R_2$;

X is —$(CH_2)_q$—, —$(CH_2)_mC(O)NH$—$(CH_2)_p$—, or —$(CH_2)_mC(O)O$—$(CH_2)_p$—;

m and p are independently chosen at each occurrence of m and p to be 1 to about 3; and q is independently chosen at each occurrence of q to be a number from 1 to about 6.

In particularly preferred methods for imaging tumors, examples of exemplary radiolabeled complex include technetium and rhenium complexes according to Formula V, VI, or VII:

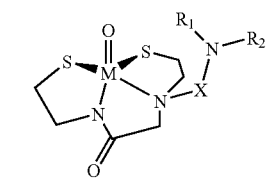

Formula V

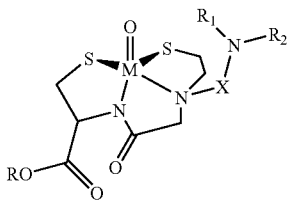

Formula VI

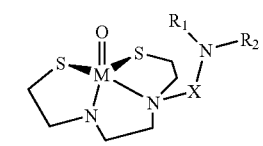

Formula VII wherein the variables of Formula V, VI and VII are defined as:

M is at least one isotope of technetium or rhenium;

R is lower alkyl group having 1 to about 8 carbon atoms, alkoxyalkyl groups having 2 to about 8 carbon atoms, or aralkyl groups having 6 to about 2 carbon atoms;

$R_1$ and $R_2$ each are independently selected from a lower alkyl group having 1 to about 4 carbon atoms; or —$NR_1R_2$ taken in combination is a heterocyclic ring according to the formula:

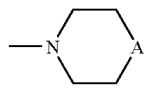

where A is $CH_2$, $NR_D$, O or S;

$R_D$ is chosen from the group consisting of hydrogen, lower alkyl group having from 1 to about 4 carbon atoms, aralkyl groups having from 7 to about 18 carbon atoms, aryl groups having 6 to about 18 carbon atoms, alkyl ester groups having about 2 to about 8 carbon atoms, aryl ester groups having about 7 to about 18 carbon atoms, alkyl amide groups having about 2 to about 8 carbon atoms, aryl amide groups having about 7 to about 18 carbon atoms, di(alkyl)aminoalkyl groups where each alkyl group has 1 to about 4 carbon atoms, —$XNR_1R_2$;

X is —$(CH_2)_q$—, —$(CH_2)_mC(O)NH$—$(CH_2)_p$—, or —$(CH_2)_mC(O)O$—$(CH_2)_p$—;

m and p are independently chosen at each occurrence of m and p to be 1 to about 3; and q is independently chosen at each occurrence of q to be a number from 1 to about 6.

The invention also includes methods for the treatment of cancer comprising the step of contacting the cancer with a cytotoxic metal complex comprising a metal ion and a compound of the following structure:

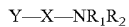

wherein

Y is a chelating ligand capable of binding the metal ion;

X is a linking group comprising a backbone chain having 1 to about 8 atoms, the backbone chain can optionally include ester, amide, amine, ether or thioether linkages in the backbone chain and does not include aromatic groups integral to the backbone chain of the linking group; and $R_1$ and $R_2$ each are independently selected from a lower alkyl group having 1 to about 4 carbon atoms, or —$NR_1R_2$ taken in combination is a heterocyclic ring having 3 to about 8 ring atoms and 1 or 2 hetero ring atoms.

Preferred treatment methods have a radioactive metal ion is a radioactive isotope. Preferred radioactive metal complexes emit alpha, beta or gamma radiation. Particularly preferred metal complexes include technetium, rhenium, yttrium, copper, gallium, indium, bismuth, platinum, and rhodium.

Preferred treatment methods of the invention have a radiolabeled therapeutic agent that comprises a compound of Formula I which comprises a tetradentate chelating ligand capable of binding a metal ion.

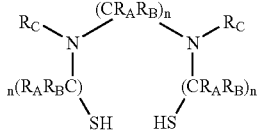

Formula I wherein $R_A$ and $R_B$ are independently chosen at each occurrence of $R_A$ and $R_B$ in the ligand from the group consisting of hydrogen, lower alkyl having 1 to about 4 carbon atoms, alkyl ester groups having about 2 to about 8 carbon atoms, aryl ester groups having about 7 to about 18 carbon atoms, alkyl amide groups having about 2 to about 8 carbon atoms, aryl amide groups having about 7 to about 18 carbon atoms, di(alkyl)aminoalkyl groups where each alkyl group has 1 to about 4 carbon atoms, and —$XNR_1R_2$; or —$(CR_AR_B)$— taken in combination is —C=O—;

$R_C$ is independently selected at each occurrence of $R_C$ from the group consisting of hydrogen, lower alkyl groups having 1 to about 8 carbon atoms, alkyl ester groups having about 2 to about 8 carbon atoms, aryl ester groups having about 7 to about 18 carbon atoms, alkyl amide groups having about 2 to about 8 carbon atoms, aryl amide groups having about 7 to about 18 carbon atoms, di(alkyl)aminoalkyl groups where each alkyl group has 1 to about 4 carbon atoms, and —$XNR_1R_2$;

X is —$(CH_2)_q$—, —$(CH_2)_mC(O)NH$—$(CH_2)_p$—, or —$(CH_2)_mC(O)O$—$(CH_2)_p$—;

m and p are independently chosen at each occurrence of m and p to be 1 to about 3;

q is independently chosen at each occurrence of q to be a number from 1 to about 6;

$R_1$ and $R_2$ each are independently selected from lower alkyl group having 1 to about 4 carbon atoms; or —$NR_1R_2$ taken in combination is a heterocyclic ring according to the formula:

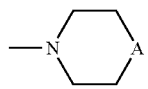

where A is $CH_2$, $NR_D$, O or S;

$R_D$ is chosen from the group consisting of hydrogen, lower alkyl group having from 1 to about 4 carbon atoms, aralkyl groups having from 7 to about 18 carbon atoms, aryl groups having 6 to about 18 carbon atoms, alkyl ester groups having about 2 to about 8 carbon atoms, aryl ester groups having about 7 to about 18 carbon atoms, alkyl amide groups having about 2 to about 8 carbon atoms, aryl amide groups having about 7 to about 18 carbon atoms, di(alkyl)aminoalkyl groups where each alkyl group has 1 to about 4 carbon atoms, —$XNR_1R_2$; and n is either 2 or 3 and is independently chosen at each occurrence of n.

Preferred radiolabeled complexes for use in the treatment method of the invention include complexes of Formula VIII:

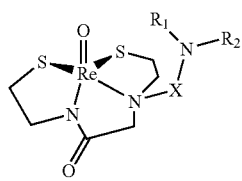

Formula VIII wherein $R_1$ and $R_2$ each are independently selected from a lower alkyl group having 1 to about 4 carbon atoms; or —$NR_1R_2$ taken in combination is a heterocyclic ring according to the formula:

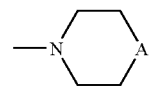

where A is $CH_2$, $NR_D$, O or S;

$R_D$ is chosen from the group consisting of hydrogen, lower alkyl group having from 1 to about 4 carbon atoms, aralkyl groups having from 7 to about 18 carbon atoms, aryl groups having 6 to about 18 carbon atoms, alkyl ester groups having about 2 to about 8 carbon atoms, aryl ester groups having about 7 to about 18 carbon atoms, alkyl amide groups having about 2 to about 8 carbon atoms, aryl amide groups having about 7 to about 18 carbon atoms, di(alkyl)aminoalkyl groups where each alkyl group has 1 to about 4 carbon atoms, —$XNR_1R_2$;

X is —$(CH_2)_q$—, —$(CH_2)_mC(O)NH—(CH_2)_p$—, —$(CH_2)_mC(O)O—(CH_2)_p$—;

m and p are independently chosen at each occurrence of m and p to be 1 to about 3; and q is independently chosen at each occurrence of q to be a number from 1 to about 6.

Examples of preferred radiolabeled complexes of the invention include technetium-99m and rhenium complexes of compounds A-D and H-M prepared in Examples 1-12. The solid state structure of complex Re-(Compound A) is shown in FIG. 1 and Example 24. While a single enantiomer of each complex is shown below, all possible stereoisomers, diastereomers, regioisomers, geometric isomers, coordination isomers, tautomers and all other isomeric forms of the complexes and compounds of the invention are contemplated and included within the scope of the invention.

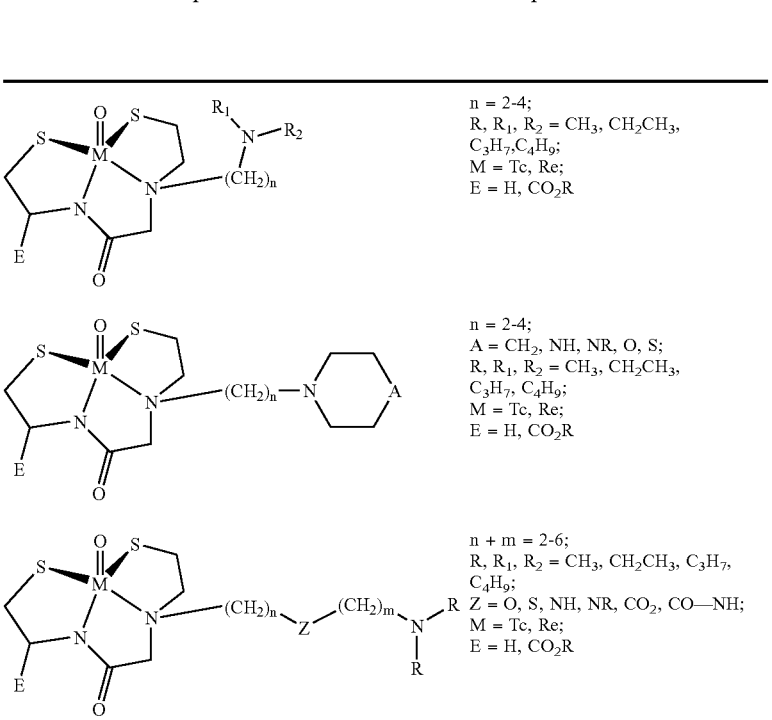

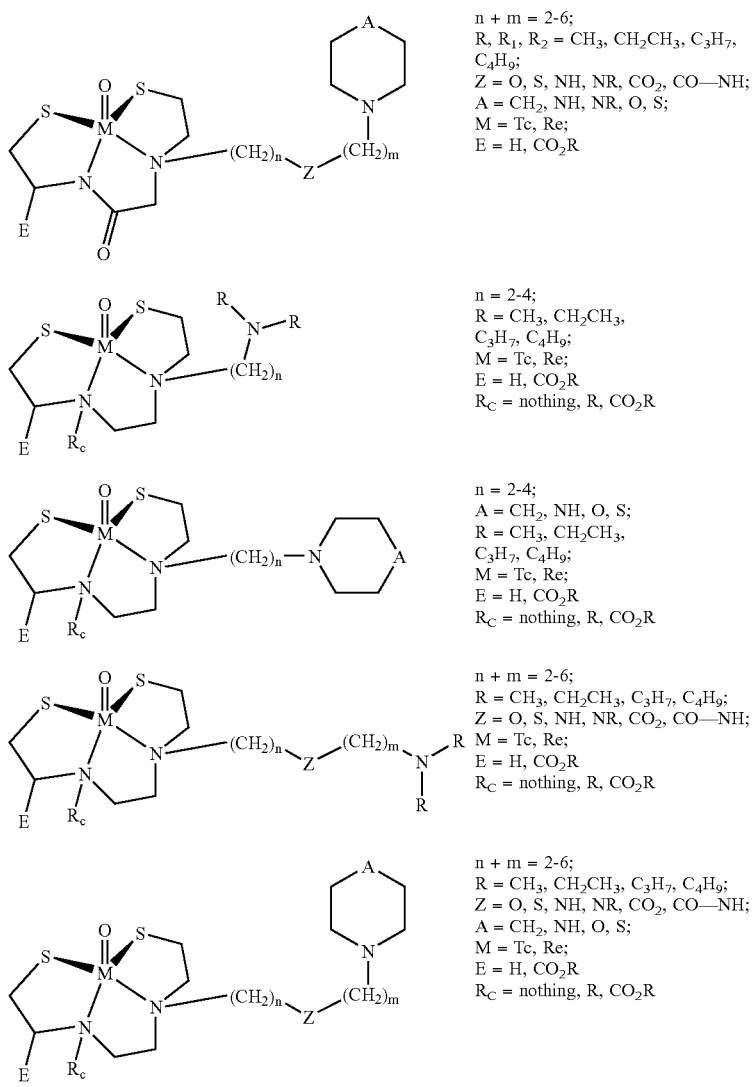

EXAMPLES

General Experimental Details:

All chemicals and reagents, obtained from commercial sources (Aldrich Chemicals, Gibco Life Technologies), were of analytical grade and were used without further purification. $^{99m}$Tc-pertechnetate was obtained via a generator (DuPont). Elemental analyses were performed on an elemental analyzer LECO-CHNS-932. $^1$H NMR spectra were obtained on a Varian XL500 MHz instrument. X-ray crystallography was performed on a Siemens platform goniometer with a CCD detector using a MoK$_\alpha$ radiation source. The structure was solved by direct methods using SHELXTL version 5.0. FT-IR spectra were recorded on a Bruker Vector 22 FTIR instrument with an ATR accessory. Mass spectra were recorded on a MicroMass LCZ electrospray LC-MS instrument. HPLC purification was performed on a Waters Millennium Chromatography System equipped with a 996 UV-VIS diode-array detector attached in series to a gamma detector consisting of a shielded photomultiplier powered by a Canberra voltage amplifier and connected to a ratemeter. For the purification of all complexes, a reversed-phase C$_8$ column equipped with a C$_{18}$ guard was eluted with methanol (solvent A) and 0.005 M phosphate-buffered saline, pH 7.4, (Sigma) (solvent B) using a linear gradient from 15:85/A:B to 90:10/A:B at a 1.0 mL/min flow rate.

Chemistry

The AADT chelate was synthesized via multi-step reactions as previously described. Chelate derivatives containing the C$_2$-linked dialkyl amino groups (Compounds A and B) as substituents were synthesized via N-alkylation of the amine nitrogen in the AADT chelate using N-(2-dialkylamino) ethyl chloride (alkyl=Et, Bu), while the C$_3$-linked dialkyl amino substituents (Compounds C and D) were incorporated in the chelate via alkylation of commercially available dialkyl amine (alkyl=Et, Bu) using a N-(3-chloropropyl)-AADT derivative (Scheme 1).

A general reaction scheme for the preparation of preferred compounds in accord with the present invention is shown in Scheme 1. The tetradentate ctelate (AADT) is alkylated with 1-chloro-3 bromopropane to form the N-3-chloropropyl substituted AADT as previously described in (Mahmood A, Kuchma M H, Goldstone J, Freiberg E, Davison A, Jones A G., "Functionalized tetradentate chelates and their Techenetium and Rhenium complexes: synthesis spectroscopy and structural characterization," in: *Technetium and rhenium in chemistry and nuclear medicine* 5, pp. 253-257 (Nicolini M, Bandoli G, Mazzi U, eds.; Padova: Servizi Grafici Editoriali) (1999), and also in Mahmood A, Wolff J A, Davison A, Jones A G., "Technetium and rhenium complexes of amine amide dithiol ligands: Ligand synthesis and metal complexes," in: *Technetium and Rhenium in Nuclear Medicine* 4, pp. 211-215 (Nicolini M, Bandoli G, Mazzi U, eds.; Verona: Cortina International) (1995), which are hereby incorporated by reference). The 3-chloro-propyl substituted AADT chelate was then reacted with a dialkyl amine to form the final dialkyl substituted propyl linked tetradentate chelate.

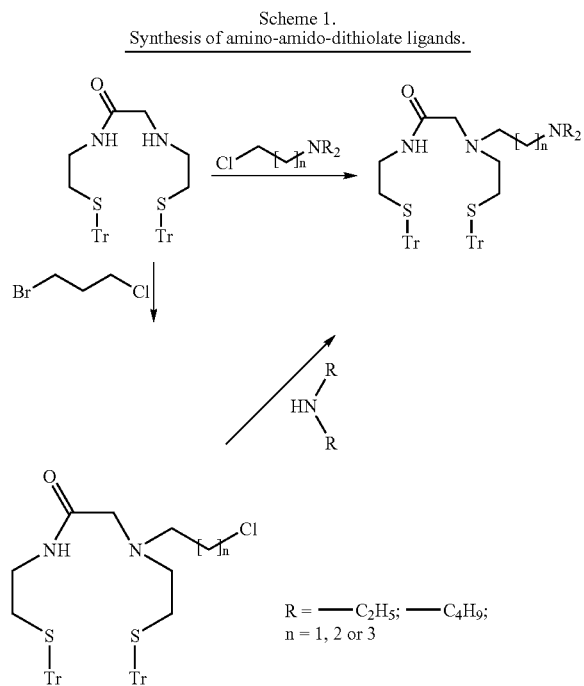

Scheme 1.
Synthesis of amino-amido-dithiolate ligands.

Technetium-99m-labeled complexes (Example 14) were synthesized by transmetallation of technetium-99m from a prereduced $^{99m}$Tc-glucoheptonate precursor (Scheme 2'). Upon heating the reaction mixture at 70° C., ligand exchange of the AADT ligand bearing the pendant tertiary amines and the $^{99m}$Tc(V)-glucoheptonate precursor yielded complexes Tc-(Complexes A-D and H-M) in nearly quantitative yields within 30 min. Typical mass amounts of the $^{99m}$Tc-complexes preclude their physical characterization; however, since both technetium and rhenium form structurally identical AADT complexes, analogous non-radioactive rhenium complexes were synthesized (vide infra) and used as surrogates for HPLC comparisons. Identical HPLC retention times established the existence of the proposed technetium-99m species.

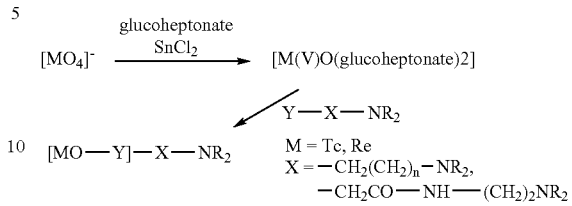

Scheme 2.
Synthesis of metal complexes of the invention by transmetallation.

Using a method similar to that for $^{99m}$Tc-complexes, the mono-oxorhenium(V) complexes (Examples 16-24) were obtained by reduction of perrhenate(VII) with stannous chloride in the presence of sodium glucoheptonate and the deprotected chelating ligand; heating the reaction mixture at 75° C. for 1 h afforded brownish-purple solids of the rhenium complexes. These complexes showed distinct $\upsilon_{Re=O}$ infrared vibrations in the 950-960 cm$^{-1}$ region, typical for mono-oxorhenium complexes. Upon chelation the N-substituent on the chelate may adopt a syn or anti configuration with respect to the asymmetric M=O core. The desheilding, anisotropic environment of the M=O core and the proximity of the N-substituent in the syn configuration to the asymmetric oxometal core results in a downfield shift of the proton resonances syn to the M=O cores thus permitting differentiation of the syn and anti diastereomers via NMR (Lever, S. Z.; Baidoo, K. E.; Mahmood, A. Structural Proof of Syn/Anti Isomerism in N-Alkylated Diaminedithiol (DADT) Complexes of Technetium. *Inorg. Chim. Acta* 1990, 176, 183-184; Francesconi, L. C.; Graczyk, G.; Wehrli, S.; Shaikh, S. N.; McClinton, D.; Liu, S.; Zubieta, J.; Kung, H. F. Synthesis and Characterization of Neutral M$^V$O (M=Tc, Re) Amine-Thiol Complexes Containing a Pendant Phenylpiperidine Group. *Inorg. Chem.*, 1993, 32, 3114-3124; O'Neil, J. P.; Wilson, S. R.; Katzenellenbogen, J. A. Preparation and Structural Characterization of Monoamine-Monoamide Bis(Thiol) Oxo Complexes of Technetium(V) and Rhenium(V). *Inorg. Chem.*, 1994, 33, 319-323; and Pelecanou, M.; Chryssou, K.; Stassinopoulou, C. I. Trends in NMR Chemical Shifts and Ligand Mobility of TcO(V) and ReO(V) Complexes with Aminothiols. *J. Inorg. Biochem.*, 2000, 79, 347-351). For example in the $^1$H NMR of the complex Re-Compound A, the methylene protons of the N-substituent (C$_7$) appear as two separate multiplets (doublets of doublets) downfield at 4.55 and 4.06 ppm, indicating a syn configuration of the N-substituent. This resonance pattern was also observed for all the complexes synthesized. Further confirmation of the syn configuration was obtained by the crystal structure determination of Re-Compound A. As expected, the structure displayed a distorted square-pyramidal geometry, with the amine-amide-dithiol donor set forming the base-plane and the oxo group at the apex of the square pyramid (FIG. 1). The rhenium atom lies slightly above the AADT base-plane. The pendant tertiary amine group connected by the C$_2$ alkyl chain was found to be oriented syn to the M=O core. Selected bond lengths and angles are listed in Table 1. While only the geometric syn isomer was formed, due to the presence of a stereogenic center at the substituted amine in the chelate, these complexes exist as enantiomeric pair's of two mirror images. Since most of the physiochemical parameters (vide infra) are not expected to be significantly different for the individual enantiomer's, they were not separated further and used as such.

The physicochemical parameters of the rhenium complexes, i.e. lipophilicity log P, log $D_{(pH\ 7.4)}$, and $pK_a$ (Table 2) were determined using HPLC methods (Braumann, T.; Grimme, L. H. Determination of Hydrophobic Parameters for Pyridazinone Herbicides by Liquid-Liquid Partition and Reversed-Phase High-Performance Liquid Chromatography. *J. Chromatogr.* 1981, 206, 7-15; Stytli, C.; Theobald, A. E. Determination of Ionization Constants of Radiopharmaceuticals in Mixed Solvents by HPLC. *Appl. Radiat. Isot.*, 1987, 38, 701-708; Johannsen, B.; Scheunemann, M.; Spies, H.; Brust, P.; Wober, J.; Syhre, R.; Pietzsch, H.-J. Technetium(V) and Rhenium(V) Complexes for 5-HT$_2$A Serotonin Receptor Binding: Structure-Affinity Considerations. *Nucl. Med. Biol.*, 1996, 23, 429-438; and Johannsen, B.; Berger, R.; Brust, P.; Pietzsch, H.-J; Scheunemann, M.; Seifert, S.; Spies, H.; Syhre, R. Structural Modification of Receptor-Binding Technetium-99m Complexes in Order to Improve Brain Uptake. *Eur. J. Nucl. Med.* 1997, 24, 316-319). As expected, the dibutyl amine group in Re-Compound B (C$_2$-linked) displays a higher log P of 3.3 compared with the diethyl-amine-containing complex Re-Compound A (C$_2$-linked) which has a log P of 1.6. Although the dibutyl groups in Re-Compound B would normally lead to a more basic amine moiety compared with Re-Compound A, both complexes have a $pK_a$=7.7. Since log $D_{(pH\ 7.4)}$ is a composite measure of log P and $pK_a$, the log $D_{(PH\ 7.4)}$ of Re-Compound B (1.9) is also higher than that of Re-Compound A (1.1). A similar log P difference was found for the C$_3$-linked complexes Re-Compound C and Re-Compound D. However, unlike Re-Compound A and Re-Compound B, the dibutyl amine complex Re-Compound D yields a slightly higher $pK_a$ of 9.5 compared with 9.2 for the diethyl-amine complex Re-Compound C. The log P of the C$_3$-linked complexes Re-Compound C and Re-Compound D is slightly lower than those of the C$_2$-linked analogues Re-Compound A and Re-Compound B, respectively. With $pK_a$ values >9 for complexes Re-Compound C and Re-Compound D, the resulting low log $D_{(PH\ 7.4)}$ values of –0.5 (Re-Compound C) and 0.7 (Re-Compound D) are not surprising, since the complexes would exist in a protonated form at pH 7.4.

Scheme 3.
Synthesis of the AADT tetradentate ligand.

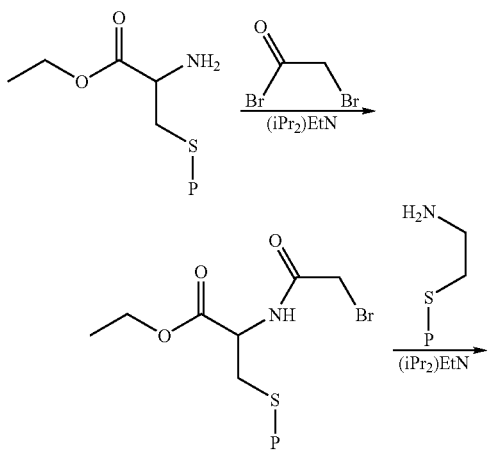

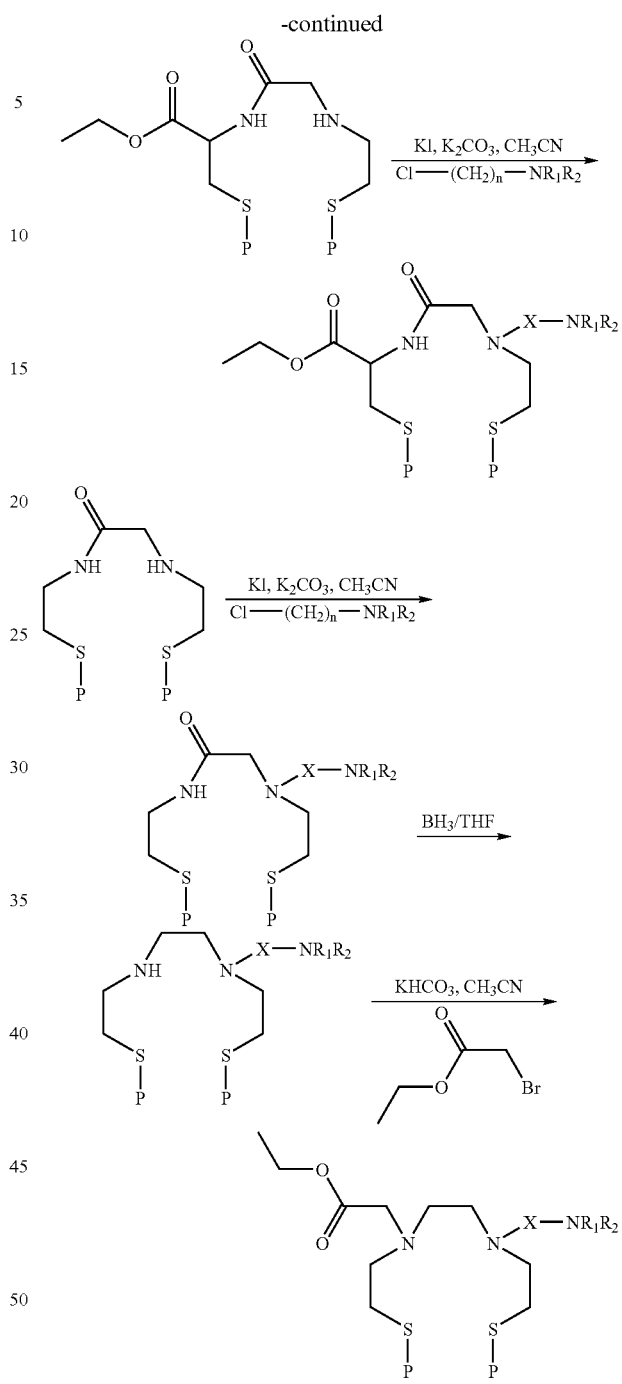

P=thiol protecting group, Trt, 4-methoxybenzyl, etc.

Compounds according to Formula III and IV were synthesized as outlined in Scheme 3. Using trityl protected cysteine ethyl ester and a procedure similar to that used to synthesize the original AADT ligand as described in Mahmood A, Wolff J A, Davison A, Jones A G., "Technetium and rhenium complexes of amine amide dithiol ligands: Ligand synthesis and metal complexes," in: *Technetium and Rhenium in Nuclear Medicine* 4, pp. 211-215 (Nicolini M, Bandoli G, Mazzi U, eds.; Verona: Cortina International) (1995), and in the references cited therein, all of which are hereby incorporated by reference. The ethyl ester derivative of AADT was subsequently alkylated with a halo-substituted tertiary amine such as 2-chloroethyl-diethylamine and refluxing the reactants in acetonitrile in the presence of K$_2$CO$_3$ and KI for 24-36 hours as described in the examples.

Other derivatives were synthesized by first protecting a compound according to Formula II with suitable thiol protecting groups incups including but not limited to 4-methoxy benzyl groups that are stable to reducing conditions and then reducing the thiol protected compound by refluxing said compound in THF in the presence of an excess of reducing agent (typically boranes such as BH$_3$, aluminum hydrides such as LiAlH$_4$, and the like). See Examples 11 and 12. These derivatives can be further alkylated with 2-bromo ethylacetate to yield additional compounds of Formula I.

Alternatively, another synthetic route was alkylation of the un-substituted AADT chelate with halo-substituted tertiary amine such as 2-chloroethyl-diethylamine or 2-chloroethyl dibutyl amine. Both procedure for the alkylation involved refluxing the reactants in acetonitrile in the presence of K$_2$CO$_3$ and KI for 24-36 hours as described in the examples.

As illustrated in Scheme 4, amido linked dialkyl substituted ligands were synthesized using a pentachlorophenyl active ester of the AADT chelate, which has been previously synthesized by us (Mahmood A, Kuchma M H, Goldstone J, Morse C, Davison A, Jones A G., "A tetradentate chelate for solid phase synthesis: Evaluation in solution and solid phase. Characterization of Technetium-99 complexes," in: *Technetium and rhenium in chemistry and nuclear medicine* 5, pp. 71-76 (Nicolini M, Bandoli G, Mazzi U, eds.; Padova: Servizi Grafici Editoriali) (1999)). Addition of the N,N-diethyl ethylene diamine to a stirring solution of the active ester in the presence of a tertiary amine base results in the formation of the product in near quantitative yields within 2 hours.

Scheme 4.
Synthesis of AADT compound H.

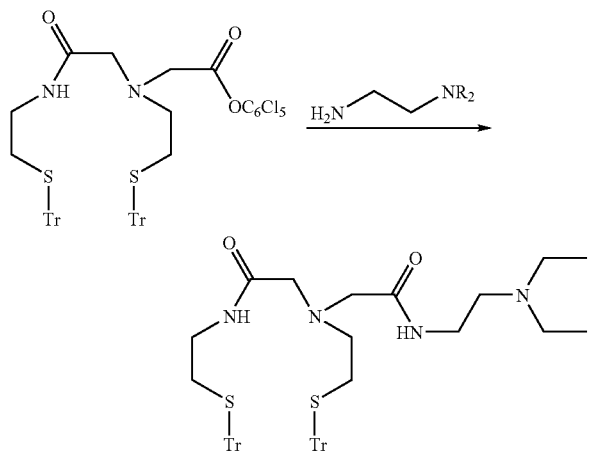

Example 1

N-[(2-diethylaminoethyl)-N-(2-(2-(S-(triphenyl-methyl)thio)ethyl)amino)acetyl]-S-(triphenylmethyl)-2-aminoethane-thiol, [AADT-(Trt)$_2$-N—CH$_2$CH$_2$—N(CH$_2$CH$_3$)$_2$] (Compound A)

N-(2-diethylamino)ethyl chloride (68.8 mg, 0.4 mmol), AADT-(Trt)$_2$ (252 mg, 0.4 mmol), KI (199.2 mg, 1.2 mmol) and K$_2$CO$_3$ (276.4 mg, 2 mmol) were added to 50 mL CH$_3$CN, and the solution was refluxed under argon atmosphere for 24 h. After cooling to room temperature, the inorganic salts were filtered, and the filtrate was evaporated to dryness. The residue was redissolved in CH$_2$Cl$_2$ and extracted with a basic (pH 11) aqueous solution. The CH$_2$Cl$_2$ portion was evaporated to a minimum volume and chromatographed on a silica-gel column with the following sequence of eluents: 100 mL CH$_2$Cl$_2$, 200 mL 1% MeOH/CH$_2$Cl$_2$, and 200 mL 2% MeOH/CH$_2$Cl$_2$. TLC (SiO$_2$): 7% NH$_3$/MeOH (5% NH$_4$OH in MeOH)/93% CH$_2$Cl$_2$. The product was isolated as a yellow viscous oil (42% yield). $^1$H NMR (CDCl$_3$) δ 7.946 (t, 1H, NH), 7.435-7.208 (m, 30H, Ar), 3.116-3.077 (q, 2H, CH$_2$), 2.94 (s, 2H, CH$_2$CO), 2.52-2.45 (m, 10H, Alkyl) 2.403 (t, 2H, CH$_2$), 2.295 (t, 2H, CH$_2$), 0.977 (t, 6H, CH$_3$); Mass Spec (MW=777.4) observed 778 (M+H)$^+$. Anal (C$_{50}$H$_{55}$N$_3$OS$_2$).½H$_2$O calcd (found): C, 76.29 (76.10); H, 7.17 (7.04); N, 5.33 (5.34).

Example 2

N-[(2-dibutylaminoethyl)-N-(2-(2-(S-(triphenylmethyl)thio)ethyl)amino)-acetyl]-S-(triphenylmethyl)-2-aminoethanethiol, [AADT-N—CH$_2$CH$_2$—N(C$_4$H$_9$)$_2$] (Compound B)

This compound was prepared analogous to the procedure previously described in EXAMPLE 1, except that N-(2-dibutylamino)ethyl chloride (0.401 mmol) was substituted for the N-(2-diethylamino)ethyl chloride. Purification was carried out on a silica-gel TLC-plate that was developed in 7% methanolic NH$_3$ (5% NH$_4$OH in MeOH)/93% CH$_2$Cl$_2$. The product was obtained as a yellowish viscous oil (38% yield). $^1$H NMR (CDCl$_3$) δ 7.829-7.745 (s, 1H, NH), 7.440-7.350 (m, 12H, Ar), 7.295-7.242 (m, 12H, Ar), 7.230-7.100 (m, 6H, Ar), 3.090-3.035 (q, 2H, —CH$_2$), 2.929 (s, 2H, —CH$_2$CO), 2.540-2.300 (m, 12H, —CH$_2$—), 2.297-2.265 (m, 2H, —CH$_2$—), 1.360 (brs, 4H, —CH$_2$—), 1.285-1.220 (m, 4H, —CH$_2$—), 0.894 (t, 6H, —CH$_3$); Mass Spec (MW=833.2) observed 834 (M+H)$^+$. Anal (C$_{54}$H$_{63}$N$_3$OS$_2$) calcd (found): C, 77.75 (77.03); H, 7.61 (7.62); N, 5.04 (5.03).

Example 3

N-[(3-diethylaminopropyl)-N-(2-(2-(S-(triphenylmethyl)thio)ethyl)amino)-acetyl]-S-(triphenylmethyl)-2-aminoethanethiol, [AADT-N—CH$_2$CH$_2$CH$_2$—N(CH$_2$—CH$_3$)$_2$] (Compound C)

AADT-N—CH$_2$CH$_2$—CH$_2$—Cl, Compound E, which is prepared according to the method described in Mahmood, A.; Kucluma, M. H.; Freiberg, E.; Goldstone, J.; Davison, A.; Jones, A. G. Functionalized Tetradentate Chelates and Their Technetium-99 and Rhenium Complexes: Synthesis, Spectroscopy and Structural Characterization. In *Technetium, Rhenium and Other Metals in Chemistry and Nuclear Medicine* 5; Nicolini, M., Mazzi, U., Eds.; Servizi Grafici Editoriali: Padova, 1999; pp 253-257, (310 mg, 0.4 mmol), diethyl amine (59.9 mg, 0.4 mmol), KI (340.1 mg, 2.1 mmol), and K$_2$CO$_3$ (141.7 mg, 1.0 mmol) were added to 50 mL CH$_3$CN, and the solution was refluxed for 24 h. The product was purified via silica-gel chromatography with 3% methanolic NH$_3$ (5% NH$_4$OH in MeOH)/97% CH$_2$Cl$_2$, yielding a yellowish oil (72% yield). $^1$H NMR (CDCl$_3$) δ 7.535-7.500 (m, 1H, —NH), 7.465-7.380 (m, 12H, Ar), 7.330-7.250 (m, 12H, Ar), 7.250-7.190 (m, 6H, Ar), 3.100-3.020 (q, 2H, —CH$_2$—), 2.896 (s, 1H, —CH$_2$CO), 2.600-2.520 (m, 4 H, —CH$_2$—), 2.500-2.400 (m, 6H, —CH$_2$—), 2.410-2.340 (m, 2H, —CH$_2$—), 2.325-2.226 (m, 2H, —CH$_2$—), 1.620-1.540 (m, 2H, —CH$_2$—), 1.025 (t, 6H, —CH$_3$); Mass Spec (MW=791.4) observed 792 (M+H)$^+$. Anal (C$_{51}$H$_{57}$N$_3$OS$_2$)).½H$_2$O calcd (found): C, 76.5 (76.65); H, 7.3 (7.24); N, 5.24 (5.30).

Example 4

N-[(3-dibutylaminopropyl)-N-(2-(2-(S-(triphenylmethyl)thio)ethyl)amino)-acetyl]-S-(triphenylmethyl)-2-aminoethanethiol, [AADT-N—CH$_2$CH$_2$CH$_2$—N(C$_4$H$_9$)$_2$] (Compound D)

Dibutyl amine (149.9 mg, 1.2 mmol), AADT-N—CH$_2$CH$_2$—CH$_2$—Cl (584 mg, 0.8 mmol), KI (664 mg, 4 mmol), and K$_2$CO$_3$ (552.8 mg, 4.0 mmol) were dissolved in 50 mL argon-saturated CH$_3$CN and refluxed for 24 h. The product was purified as a yellowish oil via silica-gel chromatography using as eluent 4% CH$_3$OH/96% CH$_2$Cl$_2$, followed by 10% CH$_3$OH/90% CH$_2$Cl$_2$ (78% yield). $^1$H NMR (CDCl$_3$) δ 7.460-7.440 (m, 1H, —NH), 7.410-7.360 (m, 12H, Ar), 7.300-7.180 (m, 18H, Ar), 3.040-3.010 (q, 2H, —CH$_2$), 2.893 (s, 2H, —CH$_2$—), 2.650-2.295 (m, 13H, —CH$_2$—), 1.900-1.380 (m, 7H, —CH$_2$—), 1.330-1.250 (m, 4H, —CH$_2$—), 0.914 (t, 6H, —CH$_3$); Mass Spec (MW=847.5) observed 848 (M+H)$^+$. Anal (C$_{55}$H$_{65}$N$_3$OS$_2$)).½H$_2$O calcd (found): C, 77.06 (77.08); H, 7.75 (7.81); N, 4.90 (5.11).

Example 5

N-(3-chloropropyl)-N-[2-(2-((S-(triphenylmethyl)thio)ethyl)amino)acetyl]-S-(triphenylmethyl)-2-aminoethanethiol, (Compound E)

This compound was synthesized as described in: Mahmood A., Kuchma M. H., Goldstone J., Freiberg E., Davison A., Jones A. G., "Functionalized tetradentate chelates and their technetium-99 and rhenium complexes: Synthesis, spectroscopy and structural characterization," in: *Technetium and Rhenium in Chemistry and Nuclear Medicine* 5, pp. 253-257 (Nicolini M., Bandoli G., Mazzi U., Eds.; SGEditoriali, Padova, Italy)(1998).

Example 6

N-(2-pentachlorophenyl acetate)-N-[2-(2-((S-(triphenylmethyl)thio)ethyl)-amino)-acetyl]-S-(triphenylmethyl)-2-aminoethanethiol, (Compound F)

This compound was synthesized as described in: Mahmood A., Kuchima M. H., Goldstone J., Morse C., Davison A., Jones A. G., "An tetradentate chelate for solid-phase synthesis: Evaluation in solution and solid phase. Characterization of technetium-99 complexes," in *Technetium and Rhenium in Chemistry and Nuclear Medicine* 5, pp. 71-76 (Nicolini M., Bandoli G., Mazzi U., Eds.; SGEditoriali, Padova, Italy)(1999).

Example 7

2-[[(2-Diethylamino-ethylcarbamoyl)-methyl]-(2-tritylsulfanyl-ethyl)-amino]-N-(2-tritylsulfanyl-ethyl)-acetamide, (Compound H)

118.2 mg (0.120 mmol) of the AADT-ligand bearing the activated ester group (Compound F, EXAMPLE 6), 14.6 mg (0.120 mmol) N,N-diethylethylene diamine and 15.5 mg (0.120 mmol) ethyl-isopropyl amine were dissolved in 8 ml of dichloromethane and stirred at room temperature for 1 h. The volatiles were removed under reduced pressure and the crude product was purified on a TLC-plate (silica gel) with CH$_2$Cl$_2$/CH$_3$OH (99:1) yielding a slightly yellowish precipitate. Yield: 94%. $^1$H NMR (CDCl$_3$, ppm): 7.45-7.38 (m, 12H, Ar), 7.32-7.18 (m, 18H, Ar), 7.07 (m, 2H, NH), 3.272 (q, 2H), 3.439 (q, 2H), 2.964 (s, 2H), 2.957 (s, 2H), 2.58-2.45 (m, 8H), 2.425 (m, 2H), 2.317 (m, 2H), 0.961 (t, 6H). Mass Spec (ES$^+$): Mol. Wt. for C$_{52}$H$_{58}$N$_4$O$_2$S$_2$: 834.4, Found 835.5 (M+H)$^+$.

Example 8

N-[(2-diethylaminoethyl)-N-(2-(2-(S-(triphenylmethyl)thio)ethyl)amino)-acetyl]-2-amino-3-(triphenylmethyl)thio-propionic acid ethyl ester, [ethyl ester-AADT-N—CH$_2$CH$_2$—N(C$_4$H$_9$)$_2$] (Compound I)

This compound was prepared analogous to the procedure previously described in EXAMPLE 1, except that the AADT chelating ligand was prepared by the synthetic method outlined in Scheme 3.
$^1$H NMR (CDCl$_3$, ppm): 7.881 (m, 1H, NH), 7.5-7.32 (m, 12H Ar), 7.32-7.12 (m, 18H Ar), 4.33 (q, 1H), 4.09 (q, 2H), 2.965 (d, 2H), 2.599 (d, 2H), 2.56-2.4 (m, 9H), 233 (m, 3H), 1.2 (t, 3H), 0.96 (t, 6H). Mass Spec (ES$^+$): Mol. Wt. for C$_{53}$H$_{59}$N$_3$O$_3$S$_2$: 849.4 Found: 850.4 (M+H)$^+$.

Example 9

N-[(2-piperidinylethyl)-N-(2-(2-(S-(triphenylmethyl)thio)ethyl)amino)-acetyl]-S-(triphenylmethyl)-2-aminoethanethiol, [AADT-N—CH$_2$CH$_2$-piperidinyl] (Compound J).

$^1$H NMR (CDCl$_3$, ppm): 7.81 (m, 1H, NH), 7.48-7.34 (m, 12H, Ar), 7.32-7.18 (m, 18H, Ar), 3.06 (q, 2H,), 2.89 (s, 2H), 2.52-2.36 (m, 7H), 2.34-2.18 (m, 7H), 1.6-1.3 (m, 6H). Mass Spec (ES$^+$): Mol. Wt. for C$_{51}$H$_{55}$N$_3$OS$_2$: 789.38, Found: 790.3 (M+H)$^+$.

Example 10

N-[(2-morpholinylpropyl)-N-(2-(2-(S-(triphenylmethyl)thio)ethyl)amino)-acetyl]-S-(triphenylmethyl)-2-aminoethanethiol, [AADT(Trt)$_2$—(CH$_2$)$_3$-morpholine] (Compound K)

This compound was prepared by the procedure outlined in Scheme 1 wherein the AADT ligand is alkylated with 1-bromo-3-chloro-propane and then aminated with morpholine in a method analogous to the method of Examples 3 and 4.
$^1$H NMR (CDCl$_3$, ppm): 7.46 (1H, NH), 7.44-7.34 (m, 12H Ar), 7.3-7.18 (m, 18H, Ar), 3.63 (m, 4H), 3.022 (q, 2H), 2.85 (s, 2H), 2.2.5-2.18 (m, 14H), 1.519 (m, 2H). Mass Spec (ES$^+$): Mol. Wt. for C$_{51}$H$_{55}$N$_3$O$_2$S$_2$: 805.37, Found: 806.7 (M+H)$^+$.

Example 11

N-[(2-morpholinylpropyl)-N-(2-(2-(S-(4-methoxybenzyl)thio)ethyl)amino)-ethyl]-S-(4-methoxybenzyl)-2-aminoethanethiol, [DADT(4-MeOBzl)$_2$—(CH$_2$)$_3$-morpholine] (Compound L)

The synthesis of the diamino-dithio chelate (Scheme 3, i.e., the reduction step that converts the amino-amido-dithiol to diamino-dithiol chelate is described in Mahmood A, Kronauge J F, Barbarics E, Madras B K, Freiberg E, Li J, Davison A, Jones A G., "Technetium(V) and rhenium(v) analogues of WAY100635 5HT$_{1a}$ receptor-binding complexes," in: *Technetium and rhenium in chemistry and nuclear medicine* 5, pp. 393-399 (Nicolini M, Bandoli G, Mazzi U, eds.; Padova: Servizi Grafici Editoriali)(1999)).

AADT(MeOBzl)$_2$-(CH$_2$)$_3$-morpholine, compound K wherein the trityl protecting groups are replaced with 4-methoxybenzyl protecting groups, (0.695 gm, 1.23 mmol) was dissolved in 20 mL of anhydrous THF under a argon atmosphere. To this solution was added a 50 mL solution of 1M BH$_3$/THF and the mixture was refluxed for 36 hrs under argon. The solution was then quenched by the slow addition of a 50:50 solution of methanol:HCl (conc.) till the evolution of gas seized. The mixture was then heated at 50° C. for 30 min., cooled to room temperature and neutralized with a 1M NaOH solution. The organics were then evaporated on a rotory evaporator and the remaining aqueous mixture was extracted with methylene chloride (3×50 mL). The methylene chloride extract was concentrated to yield a pale yellow oil, The product was purified via silica gel chromatographed, eluting with a 6% methanolic NH$_3$ (1M NH$_3$ in methanol)/94% CH$_2$Cl$_2$ to yield a pale yellow oil (34.8% yield). $^1$H NMR (CDCl$_3$, ppm): 7.2 (d, 4H, Ar), 6.82 (d, 4H, Ar), 3.76 (s, 6H, OCH$_3$), 3.72-3.55 (m, 8H), 3.2-2.7 (m, 4H), 2.7-2.2 (m, 16H), 1.6 (m, 2H). Mass Spec (ES$^+$): Mol. Wt. for C$_{29}$H$_{45}$N$_3$O$_3$S$_2$: 547.29, Found: 548.1 (M+H)$^+$.

Example 12

N-[(2-diethylaminoethyl)-N-(2-(2-(S-(4-methoxybenzyl)thio)ethyl)amino)-ethyl]-S-(4-methoxybenzyl)-2-aminoethanethiol, [DADT(4-MeOBzl)$_2$-(CH$_2$)$_2$—NEt$_2$] (Compound M)

AADT(MeOBzl)$_2$-(CH$_2$)$_2$—N(Et)$_2$, Compound A wherein the trityl protecting groups have been replaced with 4-methoxybenzyl protecting groups, (0.810 gm, 1.51 mmol) was dissolved in 20 mL of anhydrous THF under a argon atmosphere. To this solution was added a 70 mL solution of 1M BH$_3$—CS$_2$/THF and the mixture was refluxed for 36 hrs under argon. The solution was then quenched by the slow addition of a 50:50 solution of methanol:HCL (conc.) till the evolution of gas seized. The mixture was then heated at 65° C. for 30 min., cooled to room temperature and neutralized with a 1 M NaOH solution. The organics were then evaporated on a rotory evaporator and the remaining aqueous mixture was extracted with methylene chloride (3×50 mL). The methylene chloride extract was concentrated to yield a pale yellow oil, The product was purified via silica gel chromatographed, eluting with a 7% methanolic NH$_3$ (1M NH$_3$ in methanol)/93% CH$_2$Cl$_2$ to yield a pale yellow oil (57.3% yield). $^1$H NMR (CDCl$_3$, ppm): 7.25 (d, 4H, Ar), 6.85 (d, 4H, Ar), 3.808 (s, 6H, OCH$_3$), 3.69 (m, 4H), 3.2-2.4 (m, 20H), 1.026 (t, 6H). Mass Spec (ES$^+$): Mol. Wt. for C$_{28}$H$_{45}$N$_3$O$_2$S$_2$: 519.3, Found: 520.2 (M+H)$^+$.

Example 13

General Procedure for Deprotection of Trityl Protected Thiol Groups 6.0 mg of the bis-trityl-protected AADT-ligand was dissolved in 3 ml of trifluoro acetic acid and stirred at room temperature for 5 min. 1-2 drops of triethylsilyl hydride were added until the former yellowish reaction mixture became colorless.

The solvent was evaporated completely and the residue placed under high vacuum overnight.

The synthesis of the [$^{99m}$Tc] and Rhenium labeled complexes is outlined in Scheme 2.

Example 14

Technetium-99m Labeling

Technetium-99m labeling was performed using 1.0 mg of the thiol-deprotected ligands (Compound A-D, F or H-M) dissolved in 0.5 ml phosphate buffer (0.005 M, pH=7.5), which were exchange-labeled with the required activity of $^{99m}$Tc-glucoheptonate by heating the reaction at 60-75° C. for 45 min. HPLC evaluation of the technetium-99m-labeled complexes showed 80-95% radiochemical yield.

Co-injection of the characterized rhenium complexes with the analogous technetium-99m complexes showed co-elution of the radioactive species with the corresponding UV active rhenium complex.

Example 15

General Procedure for Rhenium Complexation

The bistrityl-protected ligand (Compound A-D, or H-K) (100 mg, 0.1 mmol) was dissolved in 0.25 ml anisol and 10 ml trifluoroacetic acid. The resulting yellow solution was stirred for 5 min and then titrated with triethylsilyl hydride until colorless. The solution was evaporated and placed on high vacuum till completely dry residue remained. Compounds L and M were deprotected using standard Hg(OAc)$_2$ H$_2$S procedures known in the art for the deprotection of methoxybenzyl protected thiol groups. The deprotected compounds were redissolved in 5 ml 20% MeOH in water previously argon-saturated. To this solution was added an aqueous solution of NaReO$_4$ (30 mg, 0.1 mmol) and Na-glucoheptonate (55 mg, 0.22 mmol) and, while stirring, solid SnCl$_2$ (21 mg, 0.11 mmol). The solution began to turn a brownish purple color. The pH of the reaction mixture was adjusted to 7 and the reaction was heated at 75° C. for 1 hr. The solution was then cooled to room temperature and the pH was adjusted to 8, followed by extraction with CH$_2$Cl$_2$. The CH$_2$Cl$_2$ extract was concentrated and chromatographed on silica gel, eluting with 4% MeOH in CH$_2$Cl$_2$ to yield the desired product as a pale purple solid.

Example 16

[ReOAADT]-C$_2$—NEt$_2$ (Re-Compound A). Yield: 74.4%. $^1$H NMR (CDCl$_3$) δ 4.943 (d, 1H, —CH$_2$CO), 4.554 (dd, 1H, —CH$_2$), 4.248 (d, 1H, —CH$_2$CO), 4.065 (dd, 1H, —CH$_2$), 3.993 (m, 1H, —CH$_2$), 3.639 (m, 1H, —CH$_2$), 3.532 (dd, 1H, —CH$_2$), 3.419 (ddd, 1H, —CH$_2$), 3.212 (ddd, 1H, —CH$_2$), 3.160 (ddd, 1H, —CH$_2$), 2.868 (dd, 2H, —CH$_2$), 2.795 (m, 1H, —CH$_2$), 2.570 (m, 4H, —CH$_2$), 1.579 (ddd, 1H, —CH$_2$), 1.060 (t, 6H, —CH$_3$); IR $v_{Re=O}$=952 cm$^{-1}$; Mass Spec (MW=493.1) observed 494

(M+H)⁺. Anal (C₁₂H₂₄N₃O₂ReS₂) calcd (found) C, 29.3 (29.5); H, 4.9 (5.1); N, 8.5 (8.4; S, 13.0 (12.6).

Example 17

[ReOAADT]-C₂—NBu₂ (Re-Compound B). Yield: 15%. ¹H NMR (CDCl₃): δ 4.963 (d, 1H, —CH₂CO), 4.582 (dd, 1H, —CH₂), 4.209 (d, 1H, —CH₂CO), 4.089 (dd, 1H, —CH₂), 3.975 (m, 1H, —CH₂), 3.646 (m, 1H, —CH₂), 3.492 (d, 1H, —CH₂), 3.426 (m, 1H, —CH₂), 3.264 (m, 1H, —CH₂), 3.180 (m, 1H, —CH₂), 2.899 (m, 2H, —CH₂), 2.805 (m, 1H, —CH₂), 2.464 (m, 4H, —CH₂), 1.606 (m, 1H, —CH₂), 1.450 (m, 4H, —CH₂), 1.336 (m, 4H, —CH₂), 0.943 (t, 6H, —CH₃); IR $v_{Re=O}$=958 cm⁻¹; Mass Spec (MW=549.1) observed 550 (M+H)⁺. Anal (C₁₆H₃₂N₃O₂ReS₂) calcd (found) C, 35.0 (34.9); H, 5.9 (5.7); N, 7.7 (7.7); S, 11.6 (11.9).

Example 18

[ReOAADT]-C₃—NEt₂ (Re-Compound C). Yield: 70.4%. ¹H NMR (CDCl₃) δ 4.694 (d, 1H, —CH₂CO), 4.567 (dd, 1H, —CH₂), 4.113 (d, 1H, —CH₂CO), 4.081 (dd, 1H, —CH₂), 4.000 (ddd, 1H, —CH₂), 3.610 (ddd, 1H, —CH₂), 3.399 (ddd, 1H, —CH₂), 3.239 (m, 2H, —CH₂), 3.184 (4d, 1H, —CH₂), 2.866 (dd, 1H, —CH₂), 2.555 (m, 4H, —CH₂), 2.496 (m, 2H, —CH₂), 1.921 (m, 2H, —CH₂), 1.614 (ddd, 1H, —CH₂), 1.030 (t, 6H, —CH₃); IR $v_{Re=O}$=955 cm⁻¹; Mass Spec (MW=507.1) observed 508 (M+H)⁺. Anal (C₁₃H₂₆N₃O₂ReS₂) calcd (found) C, 30.8 (30.7); H, 5.2 (5.0); N, 8.3 (8.6); S, 12.6 (12.3).

Example 19

[ReOAADT]-C₃—NBu₂ (Re-Compound D). Yield: 12.4%. ¹H NMR (CDCl₃) δ 4.698 (d, 1H, —CH₂CO), 4.564 (dd, 1H, —CH₂), 4.122 (d, 1H, —CH₂CO), 4.071 (dd, 1H, —CH₂), 3.985 (ddd, 1H, —CH₂), 3.624 (ddd, 1H, —CH₂), 3.351 (ddd, 1H, —CH₂), 3.268 (m, 2H, —CH₂), 3.202 (4d, 1H, —CH₂), 2.875 (dd, 1H, —CH₂), 2.525 (m, 4H, —CH₂), 2.512 (m, 2H, —CH₂), 1.974 (m, 2H, —CH₂), 1.645 (ddd, 1H, —CH₂), 1.389 (m, 4H, —CH₂), 0.94 (t, 6H, —CH₃); IR $v_{Re=O}$=564 cm⁻¹; Mass Spec (MW=563.2) observed 564 (M+H)⁺. Anal (C₁₇H₃₄N₃O₂ReS₂) calcd (found) C, 36.2 (36.3); H, 6.1 (6.2); N, 7.5 (7.8); S, 11.4 (11.5).

Example 20

[ReO(ethyl ester-AADT)]-C₂—N(Et)₂ (Re-Compound I)

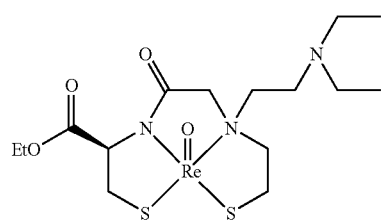

Syn Re-Compound I:
¹H NMR (CDCl₃, ppm): 5.35 (d, 1H), 4.904 (d, 1H), 4.43 (d, 1H), 4.39 (d, 1H), 4.15-4.8 (m, 3H), 3.65 (m, 1H), 3.59-3.4 (m, 3H), 2.84 (m, 3H), 2.59 (q, 4H) 1.87 (ddd, 1H), 1.21 (t, 3H), 1.08 (t, 6H). Mass Spec (ES⁺): Mol. Wt. for C₁₅H₂₈N₃O₄ReS₂: 565.1, Found: 566.0 (M+H)⁺.

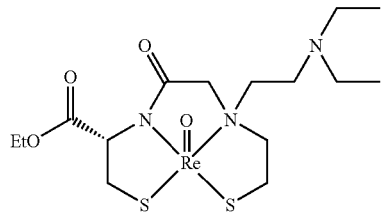

Anti Re-Compound I:
¹H NMR (CDCl₃, ppm): 5.1 (d, 1H), 4.4-4.18 (m, 4H), 3.975 (d, 1H), 3.7-3.74 (m, 2H), 3.65-3.2 (m, 3H), 3.15-2.85 (m, 3H), 2.8-2.45 (m, 4H), 1.785 (ddd, 1H), 1.3 (t, 3H), 1.103 (t, 6H). Mass Spec (ES⁺): Mol. Wt. for C₁₅H₂₈N₃O₄ReS₂: 565.1, Found: 566.0 (M+H)⁺

Example 21

[ReOAADT]-(CH₂)₂-piperidine (Re-Compound J)

¹H NMR (CDCl₃, ppm): 4.88 (d, 1H), 4.567 (m, 1H), 4.28 (d, 1H), 4.073 (m, 1H), 4.00 (m, 1H), 3.67 (m, 1H), 3.56-3.28 (m, 2H), 3.28-3.06 (m, 2H), 2.864 (ddd, 1H), 2.712 (m, 2H), 2.467 (m, 4H), 1.7-1.4 (m, 7H). Mass Spec (ES⁺): Mol. Wt. for C₁₃H₂₄ N₃O₂ReS₂: 505.09, Found: 506.0 (M+H)⁺.

Example 22

[ReOAADT]-(CH₂)₃-morpholine (Re-Compound K)

¹H NMR (CDCl₃, ppm): 4.657 (d, 1H), 4.546 (m, 1H), 4.08 (d, 1H), 4.047 (m, 1H), 4.04-3.88 (m, 1H), 3.76-3.66 (m, 4H), 3.62 (m, 1H), 3.375 (ddd, 1H), 3.3-3.04 (m, 3H), 2.856 (ddd, 1H), 2.52-2.34 (m, 6H), 2.06-1.86 (m, 2H), 1.622 (ddd, 1H). Mass Spec (ES⁺): Mol. Wt. for C₁₃H₂₄N₃O₃ReS₂: 521.08, Found: 522.4 (M+H)⁺.

Example 23

[ReODADT]-(CH2)2-N(Et)₂ (Re-Compound M)

¹H NMR (CDCl₃, ppm): 4.3-4.08 (m, 3H), 3.97 (ddd, 1H), 3.7-3.68 (m, 2H), 3.512 (ddd, 1H), 3.399 (ddd, 1H), 3.336 (m, 1H), 3.3-3.16 (m, 2H), 3.125-2.9 (m, 3H), 2.826 (dd, 1H), 2.8-2.7 (m, 4H), 1.82 (ddd, 1H), 1.156 (t, 6H). Mass Spec (ES⁺): Mol. Wt. for C₁₂H₂₆N₃OReS₂: 479.11, Found: 480.3 (M+H)⁺.

Example 24

X-Ray Structure Determination of Re-Compound A. The solid state structure as determined by X-Ray crystallography is shown in FIG. 1. Formula, C₁₂H₂₄N₃O₂ReS₂; formula weight, 493.1; unit cell dimensions, α=6.8929(8) Å; b=9.8926(12) Å; c=12.2566(14) Å; α: =93.074(2)°; β=93.770(2)°; γ=103.706(2)°; density, 2.025 mg/m³(calculated); space group, P; wave length, 0.71073 Å; reflections, 3246 (collected), 2265 (independent); absorption correction, semi-empirical from ψ-scans; refinement, full-matrix least-squares on F²; final R indices [I>2σ(I)], R1=0.0550, wR2=0.1361.

TABLE 1

Selected Bond Length and Angles of Complex Re-Compound A.

| bond length (Å) | | bond angle (°) | |
|---|---|---|---|
| Re(1)—O(1) | 1.691(8) | O(1)—Re(1)—N(1) | 118.1(4) |
| Re(1)—N(1) | 1.977(10) | O(1)—Re(1)—N(2) | 101.6(4) |
| Re(1)—N(2) | 2.172(9) | N(1)—Re(1)—N(2) | 79.9(4) |
| Re(1)—S(2) | 2.268(3) | O(1)—Re(1)—S(2) | 116.7(3) |
| Re(1)—S(1) | 2.275(3) | N(1)—Re(1)—S(2) | 124.9(3) |
| S(1)—C(1) | 1.847(13) | N(2)—Re(1)—S(2) | 83.8(2) |
| S(2)—C(6) | 1.835(12) | O(1)—Re(1)—S(1) | 106.2(3) |
| O(2)—C(3) | 1.190(14) | N(1)—Re(1)—S(1) | 82.6(3) |
| N(2)—C(4) | 1.50(2) | N(2)—Re(1)—S(1) | 151.7(3) |
| N(2)—C(5) | 1.50(2) | S(2)—Re(1)—S(1) | 88.17(11) |
| N(2)—C(7) | 1.55(2) | C(4)—N(2)—Re(1) | 109.1(7) |

Example 25

In-Vitro Tumor-Uptake Studies. Tumor-cell uptake studies in B16/F0 murine melanoma cells were performed with complexes Tc-(Compound A-D and H-M) at 37° C. and 4° C. Additionally, tumor-cell uptake of complex Tc-(Compound A) was investigated in another rapidly dividing MCF-7 human breast cancer cell line.

All compounds display a rapid cell uptake within 10 min of incubation at 37° C. (FIGS. 2-8). While the $C_2$-linked complex Tc-(Compound A) has a maximal uptake of 43%, its slightly less lipophilic $C_3$ analogue Tc-(Compound C) has a higher cell uptake of 62%. With the more lipophilic dibutyl homologues, the $C_3$-linked complex Tc-(Compound D) displaying the highest melanoma cell uptake of 68%, while its corresponding $C_2$ complex Tc-(Compound B) analogue the lowest of the entire test set (12%).

To distinguish an active uptake component from passive diffusion, measurements were also carried out at 4° C. A decrease in the incubation temperature from 37° C. to 4° C. resulted in a lower cell uptake for complexes Tc-(Compound A), Tc-(Compound C) and Tc-(Compound D) (FIGS. 2-8), with the most lipophilic complex Tc-(Compound D) showing the least difference (23% decrease) and the least lipophilic complex Tc-(Compound C) the greatest difference (77% decrease). To ensure that the decreased uptake at 4° C. is due to decreased metabolism and not cell death, the tumor cells were reincubated at 37° C. for 60 min following a 4° C. incubation; this restored the tumor-cell uptake of the complexes to the level observed at 37° C. (Table 2). These observations indicate a significant active accumulation process occurring for these compounds in melanoma cells. It is presumably the presence of this active component in the cell-uptake process at 37° C. that makes it difficult to deduce any correlations with either lipophilicity (log P and log $D_{(PH\ 7\ 4)}$) or tumor-cell uptake of these complexes.

TABLE 2

Tumor-cell uptake of complexes of the invention and a radiolabeled iodo-benzamide.

Tc-(Compound A-D)

Iodo Benzamide

% Tumor uptake (In-vitro, 60 min)

| Comp | R | N | 37° C. | 4° C. | % active | In-vivo Tumor uptake (% I.D./g, 60 min) | | | |
|---|---|---|---|---|---|---|---|---|---|
| | | | | | | Melanoma | M/Blood | M/Lung | M/Spleen |
| IBZA | Et | 2 | 26 ± 1.4 | 28 ± 1.4 | — | 5.5 | 8 | <1 | 1 |
| A | Et | 2 | 44 ± 1.6 | 33 ± 2.4 | 25 | 7/6 ± 0.6 | 7.6 | 5.4 | 4.2 |
| B | Et | 2 | 8 ± 1.9 | 16 ± 1.3 | — | 2.9 ± 0.2 | 7.6 | 2.1 | 4.0 |
| C | Et | 3 | 62 ± 0.8 | 17 ± 1.5 | 73 | 3.7 ± 0.3 | 7.7 | 2.4 | 3.0 |
| D | Et | 3 | 68 ± 2.3 | 56 ± 2.7 | 18 | 1.3 ± 0.2 | 4.3 | 1.5 | 1.4 |

Figure 5:
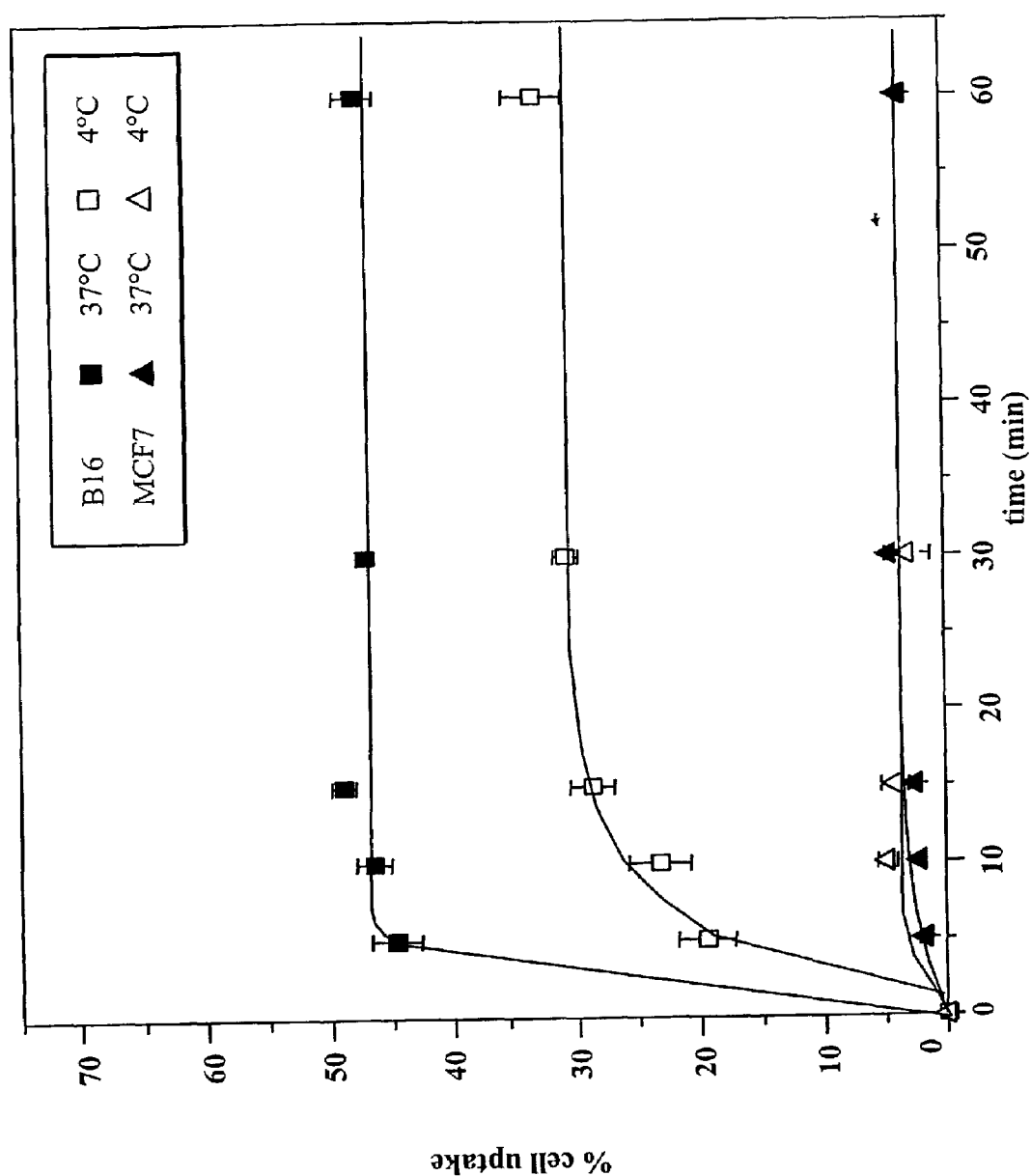
FIG. 5 is a graph illustrating the in-vitro uptake of $^{99m}$Tc-Compound A complex of the present invention in B16 melanoma cells and MCF7 breast cancer cells at different temperatures.
Figure 6:
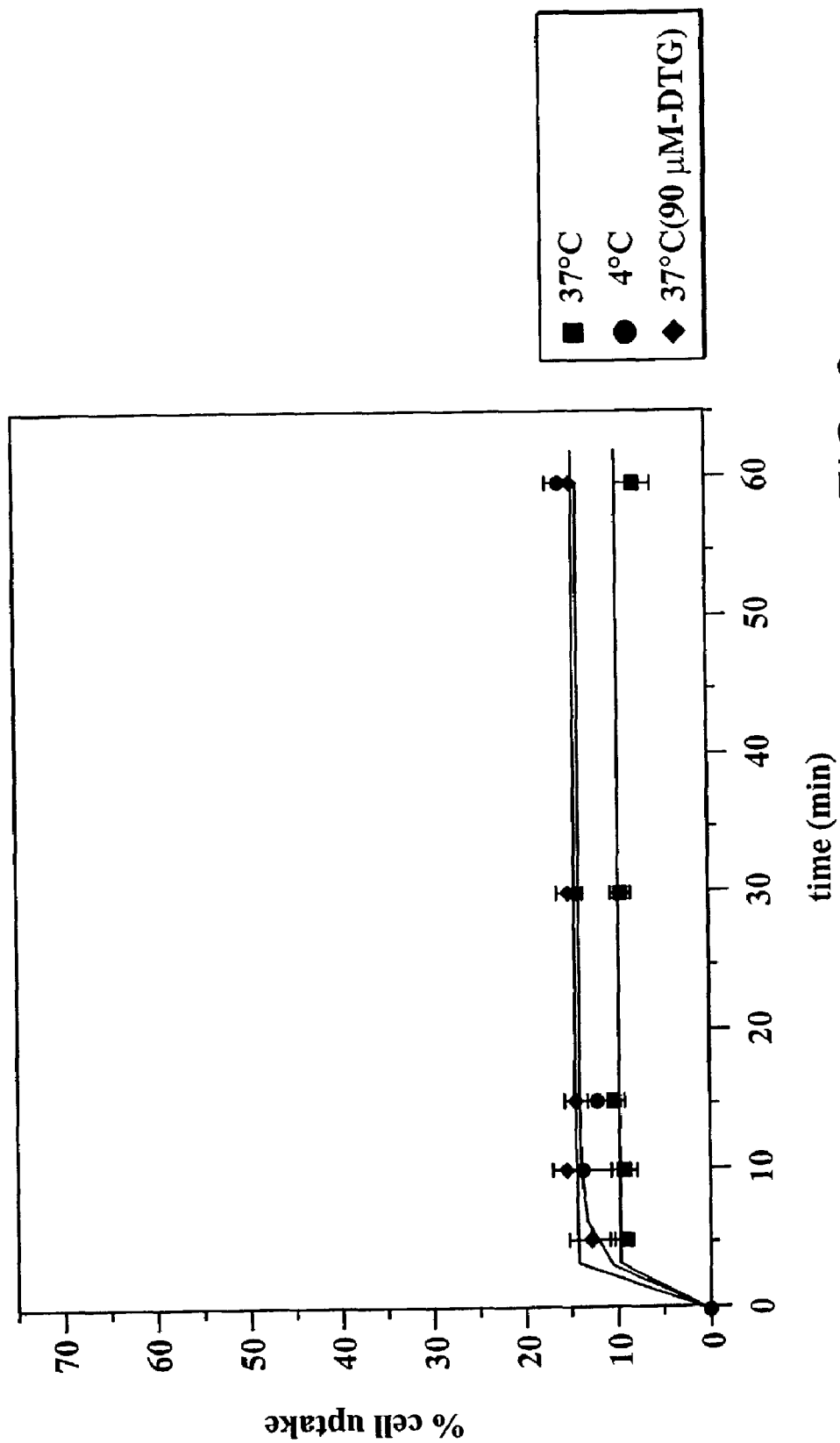
FIG. 6 is a graph illustrating the in-vitro uptake of $^{99m}$Tc-Compound B complex of the present invention in melanoma cells at different temperatures.
Figure 7:
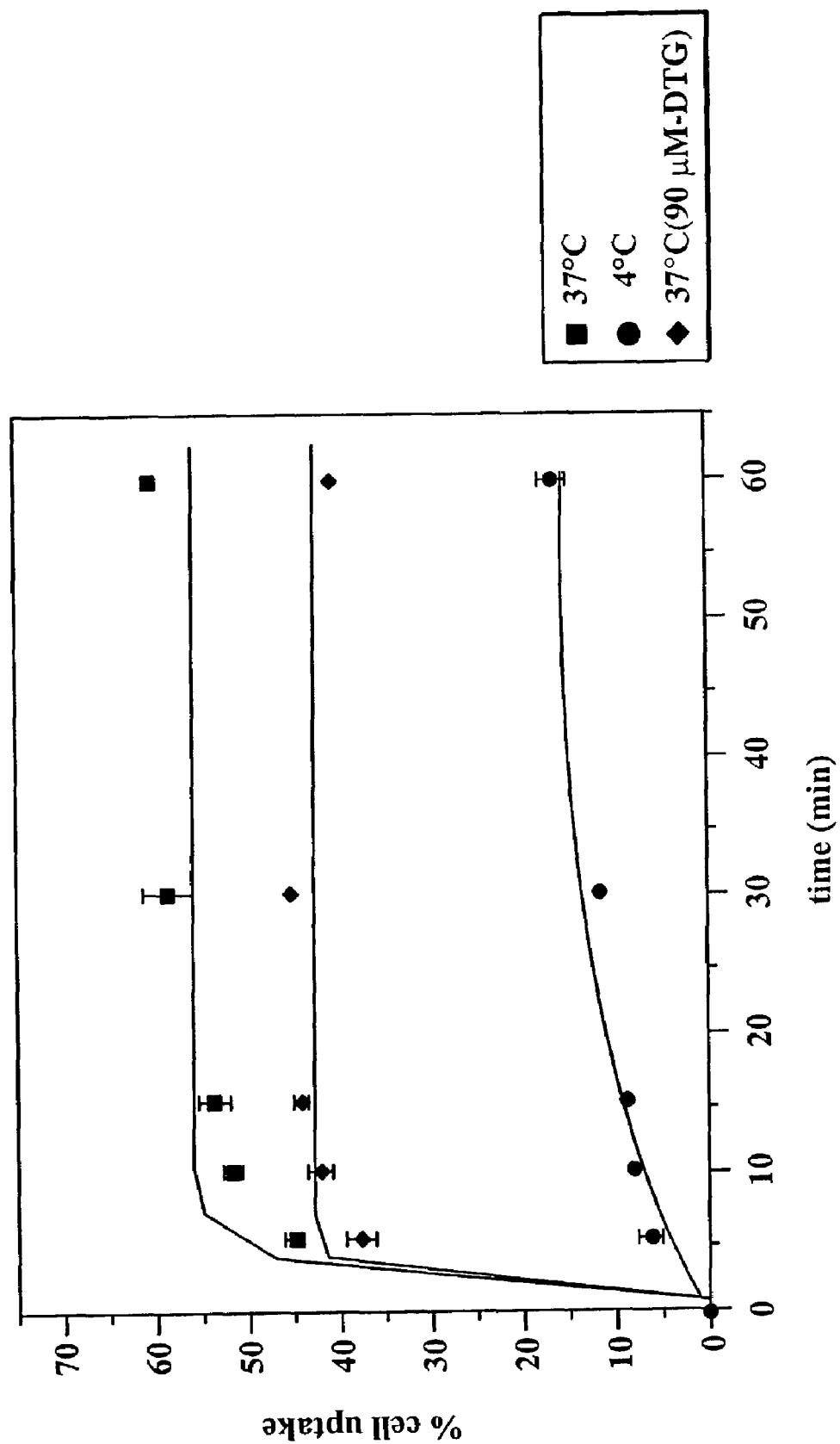
FIG. 7 is a graph illustrating the in-vitro uptake of $^{99}$Tc-Compound C complex of the present invention in melanoma cells at different temperatures.
Figure 8:
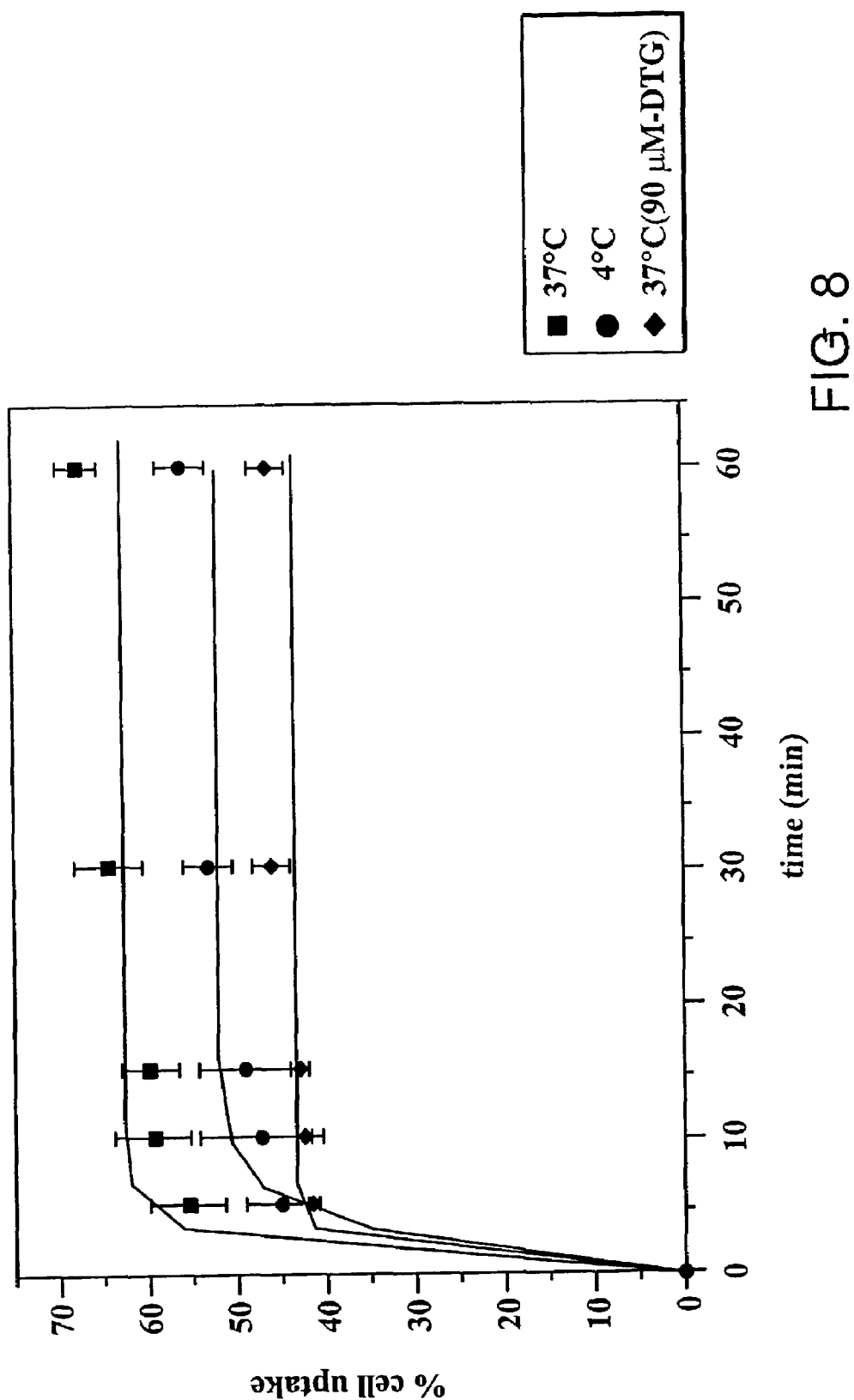
FIG. 8 is a graph illustrating the in-vitro uptake of $^{99m}$Tc-Compound D complex of the present invention in melanoma cells at different temperatures.
Figure 9:
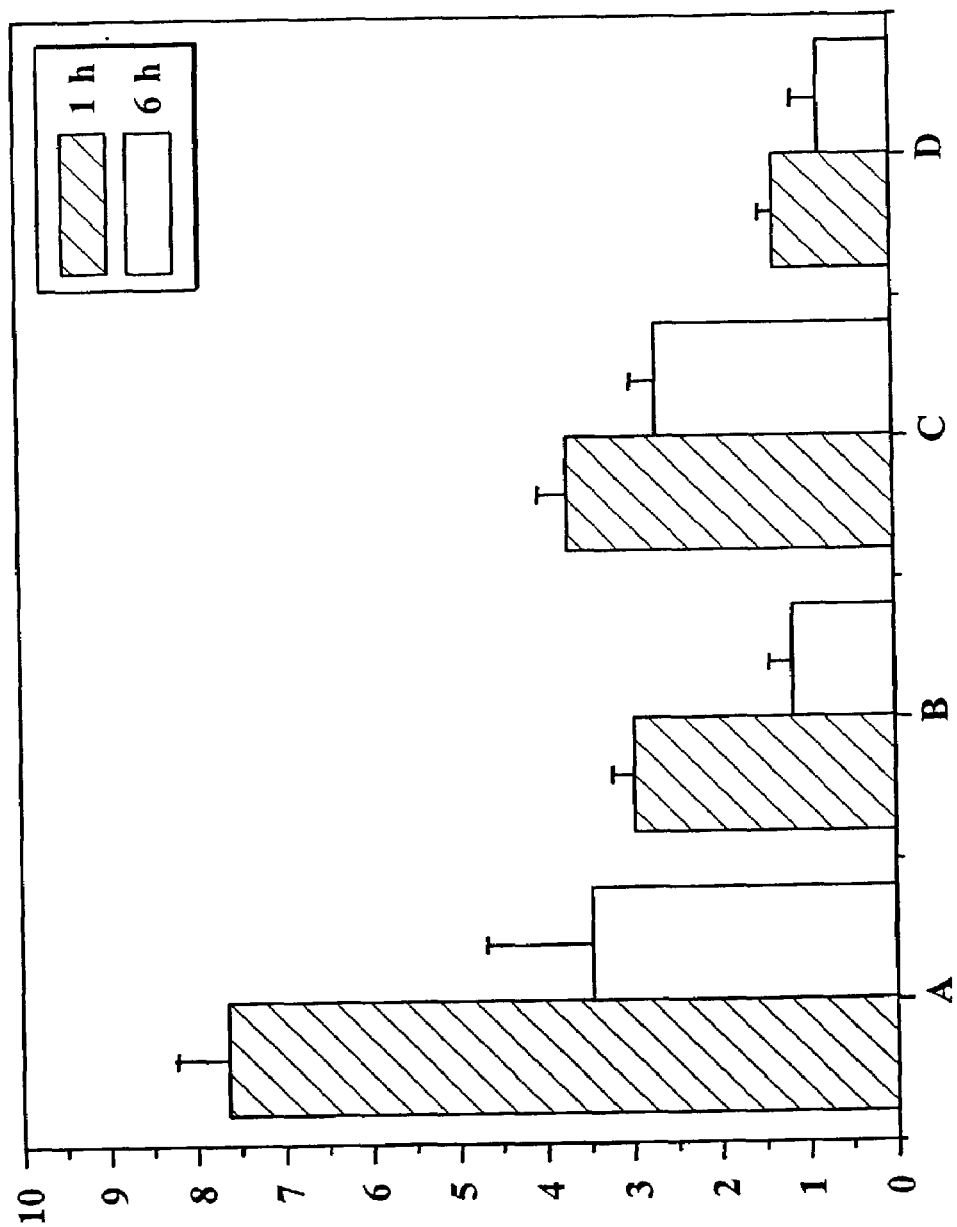
FIG. 9 is a graph illustrating the in-vivo uptake of $^{99m}$Tc-labeled complexes of the present invention in the C57/B16 mouse tumor model.
Figure 10:
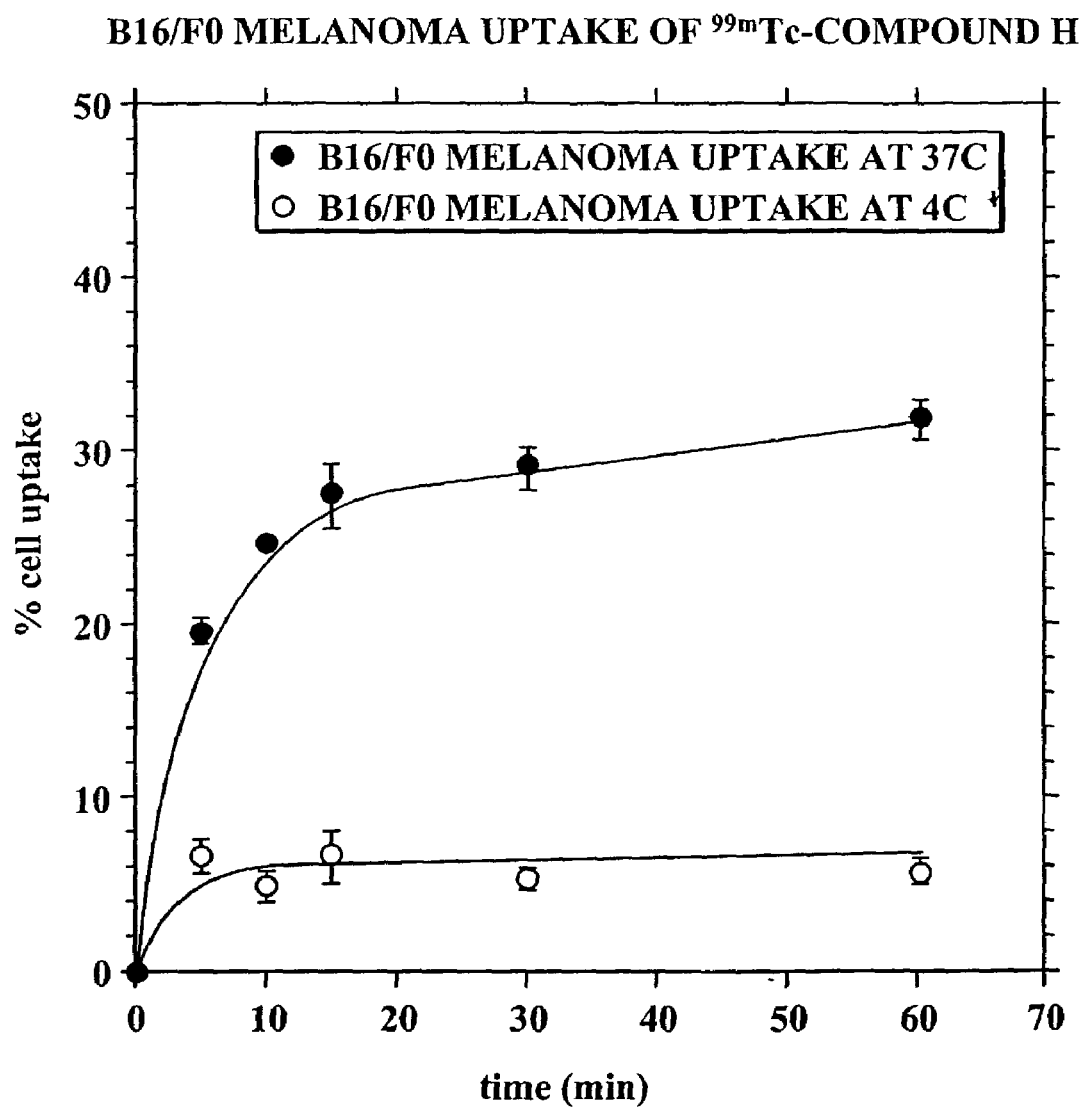
FIG. 10 is a graph illustrating the in-vitro uptake of Tc-Compound H in melanoma cells at different temperatures.
Figure 11:
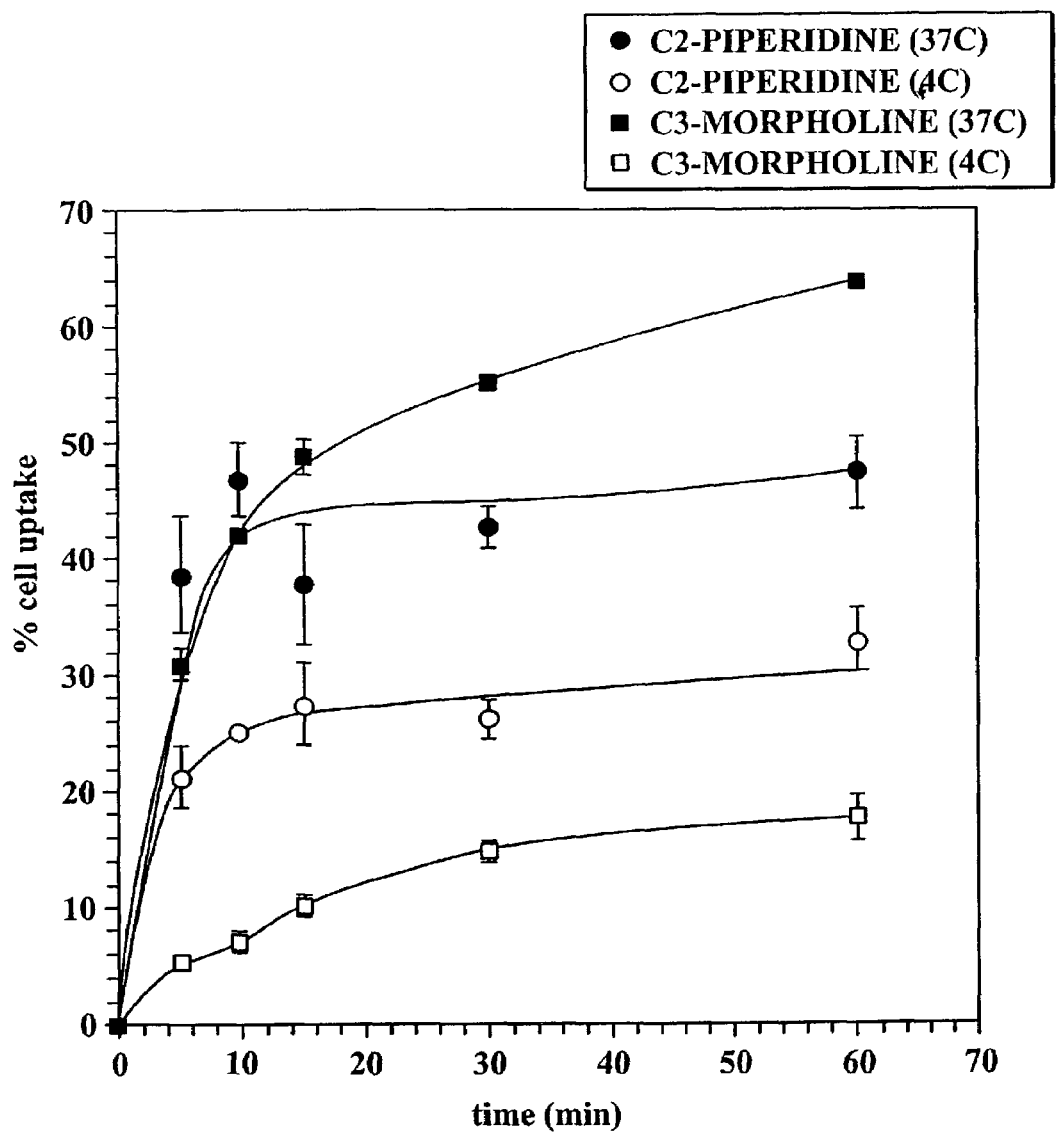
FIG. 11 is a graph illustrating the in-vitro uptake of $^{99m}$Tc-labeled complexes of the invention having a cyclic amine moiety in melanoma cells at different temperatures.
Figure 12:
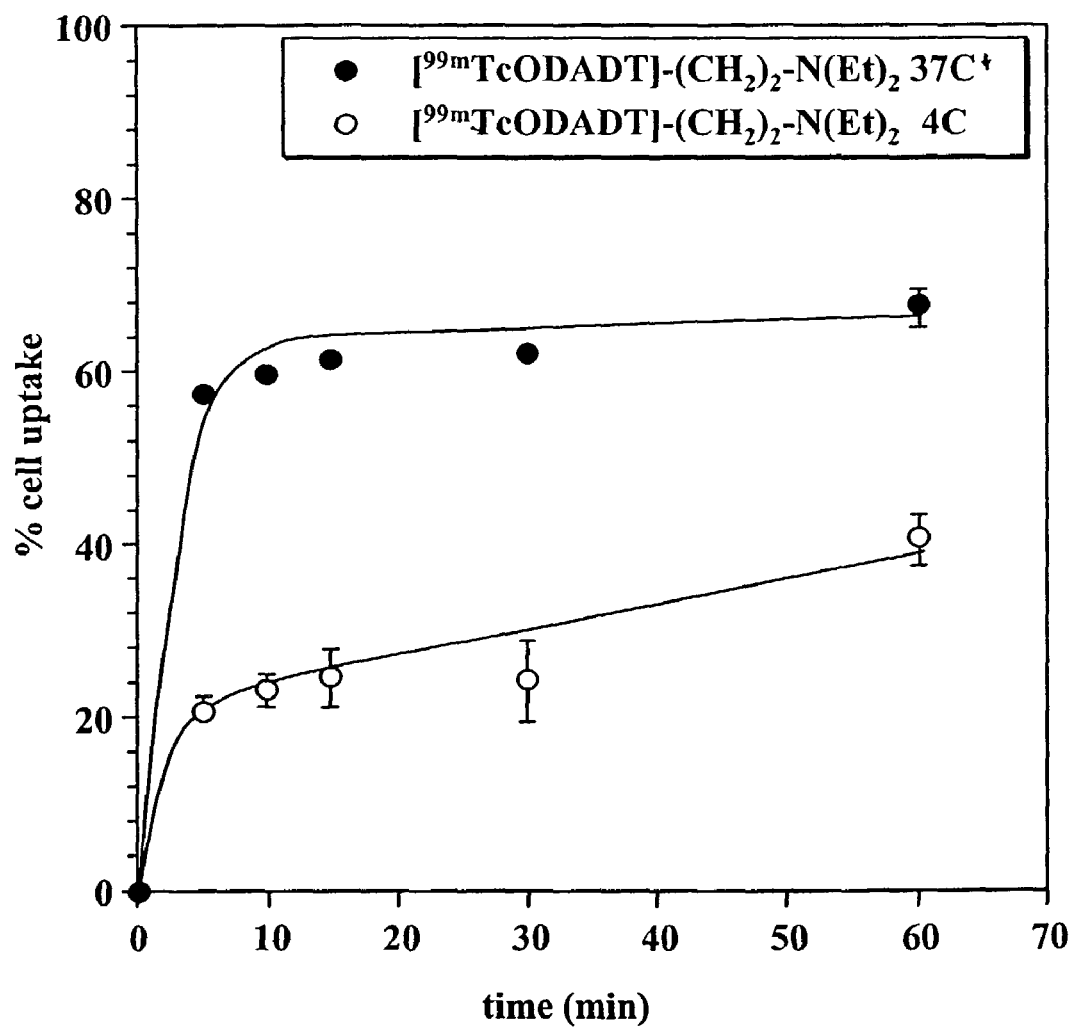
FIG. 12 is a graph illustrating the in-vitro uptake of Tc-Compound M in melanoma cells at different temperatures.
Figure 13:
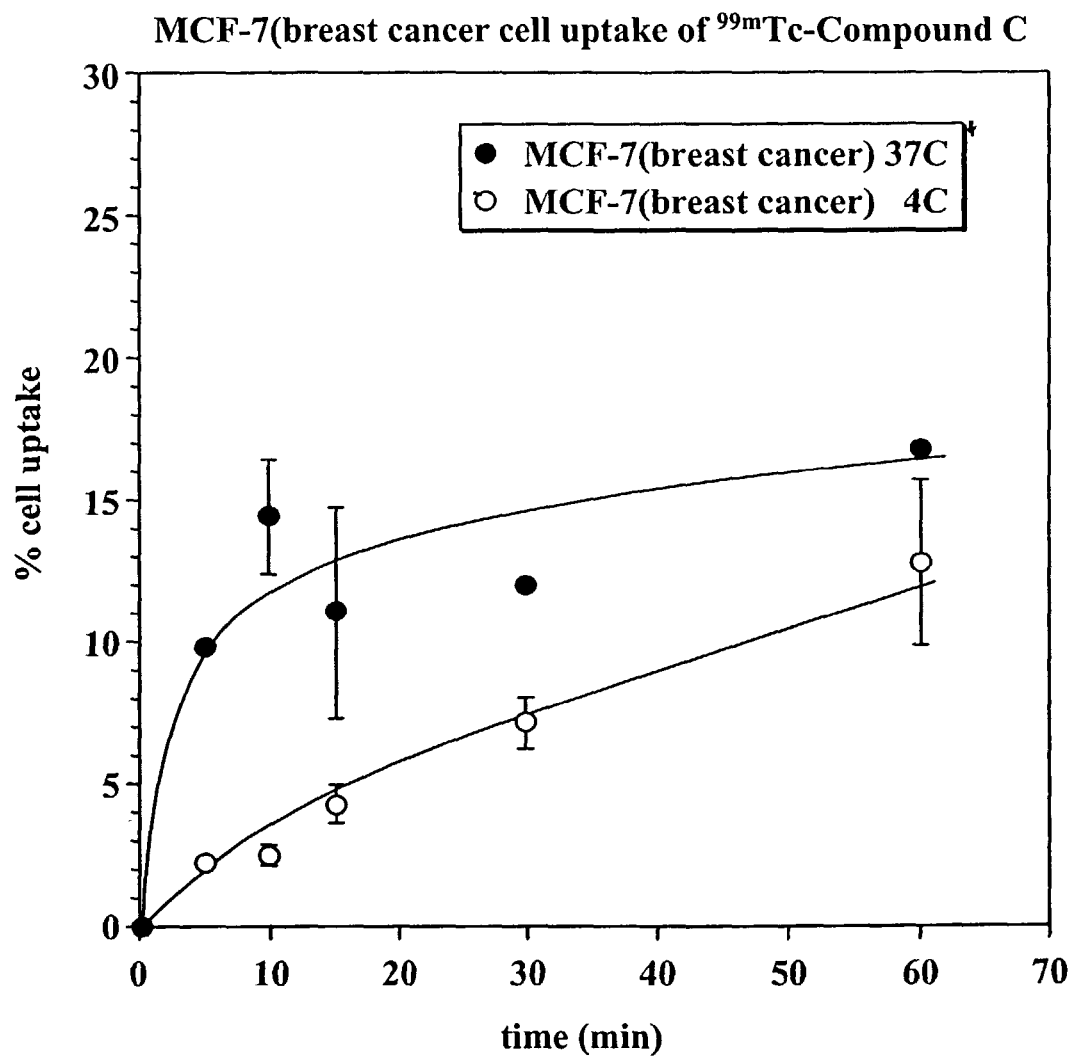
FIG. 13 is a graph illustrating the in-vitro uptake of Tc-Compound C in breast cancer cells at different temperatures.

The in-vitro uptake of complex Tc-(Compound B) is unexpectedly low for reasons not yet understood. However, complex Tc-(Compound B) exhibits the highest log P(3.3) among the four complexes and also a $pK_a$ of 7.7, making it very lipophilic at pH 7.4 as indicated by its log $D_{(pH7.4)}$ of 1.9, which may contribute to this unusual behavior. The tumor-cell uptake of complex Tc-(Compound A) in another rapidly dividing tumor-cell line MCF-7 displays a maximum cell uptake of only 6% at 37° C. compared with 43% for the B16/F0 cell line (FIG. 5). Additionally, complex Tc-(Compound C), displayed a 17% maximal uptake at 37° C. in the MCF-7 cell line (FIG. 13) compared to the 62% maximal uptake observed in the B16 melanoma cell line.

Figure 4:
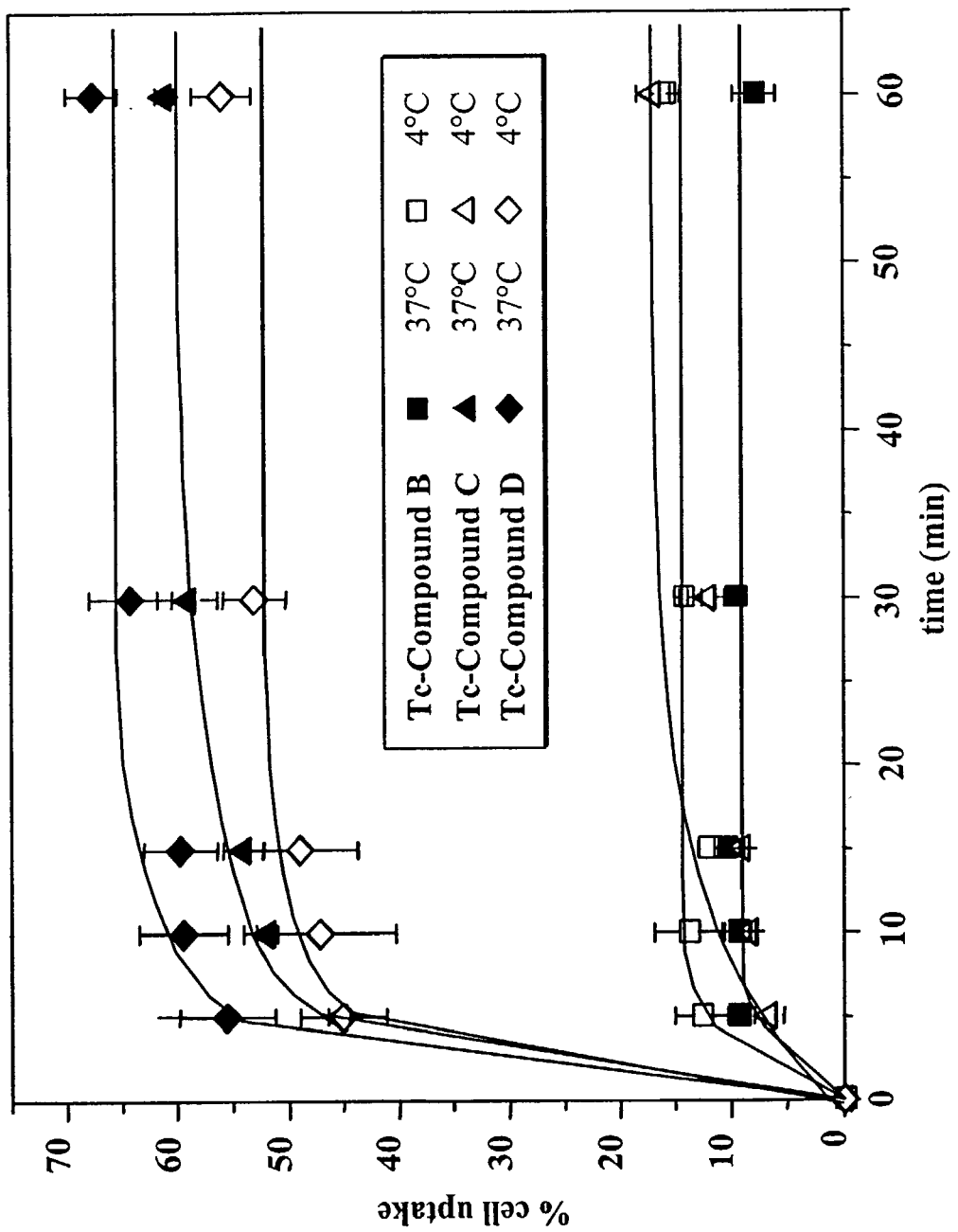
FIG. 4 is a graph illustration the in-vitro uptake of $^{99m}$Tc-labeled complexes of the present invention in melanoma cells at different temperatures.

Since the radioiodinated benzamides have been reported to possess high affinity for σ-receptors expressed by various tumors (John, C. S.; Bowen, W. D.; Saga, T.; Kinuya, S.; Vilner, B. J.; Baumgold, J.; Paik, C. H.; Reba, R. C.; Neumann, R. D.; Varma, V. M.; McAfee, J. G. A Malignant Melanoma Imaging Agent: Synthesis, Characterization, In Vitro Binding and Biodistribution of Iodine-125-(2-Piperidinylaminoethyl)-4-iodobenzamide. *J. Nucl. Med.* 1993, 34, 2169-2175; John, C. S.; Baumgold, J.; Vilner, B. J.; McAfee, J. G.; Bowen, W. D. [$^{125}$I]N-(2-Piperidinylaminoethyl)$_4$-iodobenzamide and Related Analogs as Sigma Receptor Imaging Agents; High Affinity Binding to Human Malignant Melanoma and Rat C6 Glioma Cell Lines. *J. Labelled Compd. Radiopharm.* 1994, 35, 242-244; Vilner, B. J.; John, C. S.; Bowen, W. D. Sigma-I and Sigma-2 Receptors Are Expressed in a Wide Variety of Human and Rodent Tumor Cell Lines. *Cancer Res.* 1995, 55, 408-413; and John, C. S.; Vilner, B. J.; Gulden, M. E.; Efange, S. M. N.; Langason, R. B.; Moody, T. W.; Bowen, W. D. Synthesis and Pharmacological Characterization of 4-[$^{125}$I]-N-(N-Benzylpiperidin-4-yl)-4-iodobenzamide: A High Affinity σ Receptor Ligand for Potential Imaging of Breast Cancer. *Cancer Res.* 1995, 55, 3022-3027), tumor-cell uptake studies were also performed in the presence of 1,3-di-o-tolylguanidine (DTG), a known high affinity σ-ligand. Pre-incubation of the tumor cells with DTG (90 μM), 30 min prior to the uptake experiments with the $^{99m}$Tc-complexes, yields a lower tumor-cell uptake for complexes Tc-(Compound A) (29% less), Tc-(Compound C) (33% less), and Tc-(Compound D) (32% less) at 37° C. (FIG. 4). Additional dose-response experiments conducted with intact B16/F0 cells at 37° C. with Tc-(Compound C) and DTG as the inhibitor (FIG. 3) show a DTG concentration-dependent decrease in the uptake of the complex. Complexes Tc-(Compound A), Tc-(Compound C), and Tc-(Compound D) exhibit 50% maximal inhibition at 21 μM, 49 μM, and 52 μM DTG, respectively.

Example 26

Receptor Binding Studies. To understand the involvement of receptor binding in the melanoma-cell uptake of these $^{99m}$Tc-complexes, we further investigated the affinity of these complexes in an established σ-receptor assay. Employing the structurally similar nonradioactive rhenium complexes Re-(Compound A), Re-(Compound C), and Re-(Compound D) as surrogates for the $^{99m}$Tc-complexes, competitive binding assays were carried out to determine the binding to guinea pig brain membranes ($\sigma_1$-receptors) and rat liver membranes ($\sigma_2$-receptors) to assess σ-receptor subtype selectivity, while [$^3$H]-(+)-pentazocine ($\sigma_1$) and [$^3$H]DTG/dextrallorphan ($\sigma_2$) were used as high affinity radioligands (Bowen, W. D.; de Costa, B. R.; Hellewell, S. B.; Walker, J. M.; Rice, K. C. [$^3$H]-(+)-Pentazocine: A Potent and Highly Selective Benzomorphan-Based Probe for Sigma-1 Receptors. *Mol. Neuropharmacol.* 1993, 3, 117-126; and Hellewell, S. B.; Bruce A.; Feinstein, G.; Orringer, J.; Williams, W.; Bowen, W. D. Rat Liver and Kidney Contain High Densities of $\sigma_1$ and $\sigma_2$ Receptors: Characterization by Ligand Binding and Photoaffinity Labeling. *Eur. J. Pharmacol.-Mol. Pharmacol. Sect.* 1994, 268, 9-18). The apparent $K_d$ for the radioligands are 6.44±0.53 nM ($\sigma_1$) and 23.7±2.0 nM ($\sigma_2$), respectively. All four Re-complexes, Re-(Compound A-D,) display only μM affinity towards the $\sigma_1$-receptor (Table 3). In general, their $K_i$ ($\sigma_1$) values range from 7.0 to 26.1 μM. However, unlike the iodobenzamides (Eisenhut, M.; Hull, W. E.; Mohammed, A.; Mier, W.; Lay, D.; Just, W.; Gorgas, K.; Lehmann, W. D.; Haberkorn U. Radioiodinated N-(2-Diethylaminoethyl)-benzamide Derivatives with High Melanoma Uptake: Structure-Affinity Relationships, Metabolic Fate, and Intracellular Localization. *J. Med. Chem.* 2000, 43, 3913-3922; and John, C. S.; Bowen, W. D.; Saga, T.; Kinuya, S.; Vilner, B. J.; Baumgold, J.; Paik, C. H.; Reba, R. C.; Neumann, R. D.; Varma, V. M.; McAfee, J. G. A Malignant Melanoma Imaging Agent: Synthesis, Characterization, In Vitro Binding and Biodistribution of Iodine-125-(2-Piperidinylaminoethyl)-4-iodobenzamide. *J. Nucl. Med.* 1993, 34, 2169-2175) all four complexes have a slightly higher affinity for the $\sigma_2$-receptor compared with the $\sigma_1$-receptor (Table 3). The $K_i$ values for the $\sigma_2$-receptor range from 0.18 to 2.3 μM with Re-(Compound C) displaying 100-fold greater affinity toward the $\sigma_2$-receptor subtype.

TABLE 3 pK$_a$, Lipophilicity, RP-HPLC Retention Time and σ-1 and σ-2 Receptor Affinity for the Oxorhenium(V) AADT Complexes

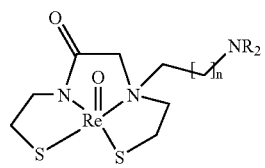

| complex | n | R | pK$_a$ | D$_{(pH 7.4)}$ | log D$_{(pH 7.4)}$ | P | log P | RP-HPLC t$_R$ (min) | σ-1[a] K$_i$ (μM) | σ-2[b] K$_i$ (μM) |
|---|---|---|---|---|---|---|---|---|---|---|
| Re-Compound | 1 | Ethyl | 7.7 | 14 | 1.1 | 38.7 | 1.6 | 30.6 | 10.9 ± 2.4 | 2.3 ± 0.3 |
| Re-Compound | 1 | n-Butyl | 7.7 | 80 | 1.9 | 2186 | 3.3 | 39.5 | n.d. | n.d. |
| Re-Compound | 2 | Ethyl | 9.2 | 0.3 | −0.5 | 19.2 | 1.3 | 35.8 | 26.1 ± 3.3 | 0.18 |
| Re-Compound | 2 | n-Butyl | 9.5 | 5 | 0.7 | 1349 | 3.1 | 40.2 | 7.8 ± 7.0 | 1.6 ± |

[a]Determined in guinea pig brain homogenate; radioligand: [$^3$H]-(+)-pentazocine.
[b]Determined in rat liver homogenate; radioligand: [$^3$H]DTG in presence of 1 μM dextrallorphan to mask σ$_1$ receptors.

TABLE 4

Biodistribution and Tumor/Nontumor Ratios of Complexes
Tc-(Compound A–D) at 1 and 6 Hours Post-injection[a,b]

| organ | A 1 h | | A 6 h | | B 1 h | | B 6 h | | C 1 h | | C 6 h | | D 1 h | | D 6 h | |
|---|---|---|---|---|---|---|---|---|---|---|---|---|---|---|---|---|
| blood | 1.00[b] | ±0.4 | 0.32 | ±0.1 | 0.39 | ±0.0 | 0.13 | ±0.0 | 0.48 | ±0.1 | 0.14 | ±0.0 | 0.31 | ±0.1 | 0.09 | ±0.0 |
| heart | 0.82 | ±0.3 | 0.11 | ±0.0 | 0.32 | ±0.2 | 0.07 | ±0.0 | 0.38 | ±0.2 | 0.02 | ±0.0 | 0.27 | ±0.1 | 0.04 | ±0.0 |
| lung | 1.40 | ±0.4 | 0.47 | ±0.2 | 1.39 | ±0.4 | 0.27 | ±0.1 | 1.55 | ±0.7 | 0.21 | ±0.0 | 0.86 | ±0.3 | 0.24 | ±0.1 |
| spleen | 1.83 | ±0.5 | 0.34 | ±0.1 | 0.73 | ±0.1 | 0.17 | ±0.0 | 1.24 | ±0.3 | 0.14 | ±0.0 | 0.92 | ±0.2 | 0.34 | ±0.0 |
| liver | 12.7 | ±1.5 | 4.08 | ±0.9 | 10.9 | ±0.5 | 5.66 | ±0.5 | 14.6 | ±1.8 | 6.42 | ±1.1 | 6.83 | ±0.9 | 2.45 | ±1.1 |
| kidney | 5.53 | ±0.8 | 1.98 | ±0.2 | 6.78 | ±1.1 | 3.30 | ±0.5 | 5.62 | ±0.4 | 2.97 | ±0.4 | 3.49 | ±0.6 | 2.00 | ±0.8 |
| muscle | 0.35 | ±0.2 | 0.08 | ±0.0 | 0.98 | ±0.3 | 0.06 | ±0.0 | 0.38 | ±0.1 | 0.06 | ±0.0 | 0.13 | ±0.0 | 0.05 | ±0.0 |
| brain | 0.30 | ±0.1 | 0.05 | ±0.0 | 0.16 | ±0.0 | 0.01 | ±0.0 | 0.08 | ±0.0 | 0.01 | ±0.0 | 0.04 | ±0.0 | 0.01 | ±0.0 |
| melanoma | 7.62 | ±0.6 | 3.45 | ±1.2 | 2.95 | ±0.2 | 1.14 | ±0.26 | 3.70 | ±0.3 | 2.67 | ±0.2 | 1.31 | ±0.1 | 0.80 | ±0.2 |
| mel/blood | 7.6 | ±0.54 | 10.8 | ±1.00 | 7.6 | ±0.33 | 8.8 | ±0.32 | 7.7 | ±0.43 | 19.1 | ±0.33 | 4.2 | ±0.21 | 8.9 | ±0.10 |
| mel/spleen | 4.2 | ±0.58 | 10.1 | ±1.11 | 4.0 | ±0.80 | 6.7 | ±0.24 | 3.0 | ±0.30 | 19.1 | ±0.28 | 1.4 | ±0.34 | 2.4 | ±0.09 |
| mel/lung | 5.4 | ±0.60 | 7.3 | ±0.98 | 2.1 | ±0.81 | 4.2 | ±0.22 | 2.4 | ±1.00 | 12.7 | ±0.22 | 1.5 | ±0.41 | 3.3 | ±0.16 |
| mel/liver | 0.6 | ±0.09 | 0.9 | ±0.35 | 0.3 | ±0.03 | 0.2 | ±0.18 | 0.3 | ±0.08 | 0.4 | ±0.2 | 0.2 | ±0.15 | 0.3 | ±0.19 |

[a] n = 4 animals per time point.
[b] Values represent % ID/g wet tissue.

TABLE 5

Biodistribution of [99mTcOAADT]-(CH2)$_n$-cyclic amines

| compound | 99mTc-Compound J | | | | 99mTc-Compound K | | | |
|---|---|---|---|---|---|---|---|---|
| organ | 1 h | | 6 h | | 1 h | | 6 h | |
| blood | 2.26 | ±0.58 | 0.20 | ±0.05 | 0.34 | ±0.12 | 0.08 | ±0.01 |
| heart | 0.91 | ±0.42 | 0.26 | ±0.32 | 0.39 | ±0.21 | 0.07 | ±0.02 |
| lung | 2.50 | ±0.54 | 0.31 | ±0.12 | 0.49 | ±0.20 | 0.10 | ±0.09 |
| spleen | 3.28 | ±2.44 | 0.20 | ±0.01 | 0.46 | ±0.24 | 0.08 | ±0.05 |
| liver | 14.9 | ±5.16 | 4.62 | ±0.62 | 11.0 | ±1.81 | 3.98 | ±0.78 |
| kidney | 4.26 | ±0.98 | 2.31 | ±0.30 | 2.03 | ±0.64 | 0.59 | ±0.10 |
| muscle | 0.42 | ±0.28 | 0.15 | ±0.14 | 0.26 | ±0.18 | 0.05 | ±0.03 |
| brain | 0.52 | ±0.45 | 0.05 | ±0.02 | 0.06 | ±0.02 | 0.01 | ±0.01 |
| melanoma | 5.26 | ±0.30 | 3.33 | ±0.74 | 4.48 | ±1.13 | 3.83 | ±0.79 |
| mel./blood | 2.3 | | 16.7 | | 13.2 | | 47.9 | |
| mel./spleen | 1.6 | | 16.7 | | 9.7 | | 47.9 | |
| mel./lung | 2.1 | | 10.7 | | 9.1 | | 38.3 | |
| mel./liver | <1 | | <1 | | <1 | | 1 | |

The apparent low σ-receptor affinity of the Re complexes, Re-(Compound A-D), the low tumor cell uptake in the MCF-7 cells, known to express σ$_2$ receptors (John, C. S.; Bowen, W. D.; Saga, T.; Kinuya, S.; Vilner, B. J.; Baumgold, J.; Paik, C. H.; Reba, R. C.; Neumann, R. D.; Varma, V. M.; McAfee, J. G. A Malignant Melanoma Imaging Agent: Synthesis, Characterization, In Vitro Binding and Biodistribution of Iodine-125-(2-Piperidinylaminoethyl)-4-iodobenzamide. *J. Nucl. Med.* 1993, 34, 2169-2; and Vilner, B. J.; John, C. S.; Bowen, W. D. Sigma-1 and Sigma-2 Receptors Are Expressed in a Wide Variety of Human and Rodent Tumor Cell Lines. *Cancer Res.* 1995, 55, 408-413), and the high micromolar concentrations of DTG required to inhibit the tracer concentration of the $^{99m}$Tc-complex uptake in intact B16 melanoma cells, would seem to suggests that, while binding to the σ-receptors cannot be excluded from the accumulation process, the inhibitory effects observed in the intact B16 cell-uptake assay may be due to secondary effects induced by DTG on the growth and proliferation of the B16 melanoma cells (Vilner, B. J.; de Costa, B. R.; Bowen, W. D. Cytotoxic Effects of Sigma Ligands: Sigma Receptor-Mediated Alterations in Cellular Morphology and Viability. *J. Neurosci.* 1995, 15, 117-134; and Brent, P. J.; Pang, G. T. σ-Binding Site Ligands Inhibit Cell Proliferation in Mammary and Colon Carcinoma Cell Lines and Melanoma Cells in Culture. *Eur. J. Pharmacol.* 1995, 278, 151-160), and that as recently shown with the radioiodinated benzamides, other factors such as melanin production and content may play a more significant role in the accumulation of these complexes in melanomas.

Example 27

In-Vivo Tumor Uptake. To study the tumor uptake of $^{99m}$Tc-complexes, Tc-(Compound A-D and J-K), in vivo, biodistribution experiments at 1 h and 6 h after their administration were carried out in C57B16 mice with palpable B16 melanoma nodules. The biodistribution data including melanoma/nontumor (M/NT) ratios for selected organs are summarized in Table 4 and 5 as percentage injected dose per gram (% ED/g).

Complex Tc-(Compound A) displays the highest tumor uptake of the entire test set with 7.6% ID/g and high melanoma/blood (M/B) (7.6), melanoma/spleen (M/S) (4.2) and melanoma/lung (M/L) (5.4) ratios at 1 h after administration. Although the % fD/g in the tumor decreases at 6 h after administration (3.5% ID/g), the M/NT ratios increase for blood (10.8), spleen (10.1) and lung (7.3) due to the faster clearance of the complex from these tissues compared with the tumor. In comparison, complex Tc-(Compound B), the more lipophilic (log D$_{(pH\ 7\ 4)}$=1.9) analogue, yields a lower melanoma uptake of 3.0% ID/g 1 h after administration. While the total tumor uptake is significantly lower than that for Tc-(Compound A), the M/NT ratios are equivalent (except for a lower M/L value of 2.1) at the 1-h time point. At 6 h after administration, although the M/NT ratios increase, the lower tumor content of complex Tc-(Compound B) (1.1% ID/g) may be inadequate for in-vivo imaging.

Complex Tc-(Compound C) displays a melanoma uptake of 3.7% ID/g at 1 h after administration, and M/NT ratios almost identical with those for complexes Tc-(Compound A) and Tc-(Compound B) (except for M/L). However, a greater retention in tumor tissue and a faster clearance from non-tumor tissues result in a significant increase in the M/NT ratios for Tc-(Compound C) at the 6-h point, giving M/B, M/S and M/L ratios of 19, 19, and 12.7, respectively. The melanoma uptake of complex Tc-(Compound D) (1.3% ID/g 1 h after administration) and the M/NT ratios are the lowest of the test set and may be far from ideal for in-vivo diagnostic purposes.

A complex wherein log $D_{(pH\ 7.4)}=1$ seems to favor a higher melanoma uptake of $^{99m}$Tc-complexes Tc-(Compound A-D). However, the more rigid tetradentate $^{99m}$Tc-AADT complexes, such as Tc-(Compound A), possess a $pK_a=7.7$ and display a higher in-vivo melanoma uptake.

Example 28

Determination of Lipophilicity and $pK_a$ Values. The lipophilicity and $pK_a$ values of all complexes were determined using HPLC methods described previously (Stylli, C.; Theobald, A. E. Determination of Ionization Constants of 4 Radiopharmaceuticals in Mixed Solvents by HPLC. *Appl. Radiat. Isot.*, 1987, 38, 701-708; Johannsen, B.; Scheunemann, M.; Spies, H.; Brust, P.; Wober, J.; Syhre, R.; Pietzsch, H.-J. Technetium(V) and Rhenium(V) Complexes for 5-HT$_{2A}$ Serotonin Receptor Binding: Structure-Affinity Considerations. *Nucl. Med. Biol.*, 1996, 23, 429-438; and Johannsen, B.; Berger, R.; Brust, P.; Pietzsch, H.-J.; Scheunemann, M.; Seifert, S.; Spies, H.; Syhre, R. Structural Modification of Receptor-Binding Technetium-99m Complexes in Order to Improve Brain Uptake. *Eur. J. Nucl. Med.* 1997, 24, 316-319). Log P, log $D_{(pH\ 7.4)}$ and $pK_a$ values were determined on a Perkin-Elmer HPLC system 1020 using a reversed phase PRP-1 column (250×4.1 mm; 10 µm; Hamilton) run under isocratic conditions with a flow rate of 1.5 mL/min at room temperature. The mobile phase was acetonitrile:phosphate buffer (0.01 M), 3:1, v/v, with the aqueous buffer adjusted to the desired pH between 3 and 11. The capacity factor (k') was calculated for each determination (Braumann, T.; Grimme, L. H. Determination of Hydrophobic Parameters for Pyridazinone Herbicides by Liquid-Liquid Partition and Reversed-Phase High-Performance Liquid Chromatography. *J. Chromatogr.* 1981, 206, 7-15; El Tayer, N.; van der Waterbeemd, H.; Testa, B. Lipophilicity Measurements of Protonated Basic Compounds by Reversed-Phase High-Performance Liquid Chromatography. II. Procedure for the Determination of a Lipophilic Index Measured by Reversed-Phase High Performance Liquid Chromatography. *J. Chromatogr.* 1985, 320, 305-312; and Minick, D. J.; Frenz, J. H.; Patrick, M. A.; Brent, D. A. A Comprehensive Method for Determining Hydrophobicity Constants by Reversed-Phase High-Performance Liquid Chromatography. *J. Med. Chem.*, 1988, 31, 1923-1933) and the partition coefficient at a given pH (D or log D) were calculated from the equation: log D=a log k'+b where the parameters a and b are predetermined using standard amines. The fitted points of inflection from the sigmoidal $D_{HPLC}$/pH profiles permit calculation of the $pK_{HPLC}$(Stylli, C.; Theobald, A. E. Determination of Ionization Constants of Radiopharmaceuticals in Mixed Solvents by HPLC. *Appl. Radiat. Isot.*, 1987, 38, 701-708). The aqueous ionization constants $pK_a$ were calculated from the $pK_{HPLC}$ values after correction with a predetermined correction factor obtained using standard amine compounds. Log P values of the neutral complexes were estimated from the respective upper plateau of the sigmoidal log D/pH curve in the alkaline range.

Example 29

In-Vitro Cell Studies. Murine B16/F0 melanoma cells and human MCF-7 breast cancer cells were obtained from American Type Culture Collection, Manassas Va., (ATCC) and were grown in T-175 flasks in 14 mL Dulbecco's Modified Eagle Medium (D-MEM; Gibco, Life Technology, Gaithersburg, Md.) containing 4500 mg/L D-glucose, L-glutamine, and pyridoxine hydrochloride, 110 mg/L sodium pyruvate, 10% fetal bovine serum (FBS), 0.2% gentamicin and 0.5% penicillin-streptomycin solution. All cells were harvested from cell culture flasks by trypsinization with 1 mL trypsin-EDTA solution (0.25% trypsin, 1 mM EDTA×4 Na) (Gibco). After being washed with 12 mL Dulbecco's Phosphate-Buffered Saline (PBS) (Gibco), pH 7.2 ($Ca^{2+}$- and $Mg^{2+}$-free; g/L KCl, 0.20; $KH_2PO_4$, 0.20; NaCl, 8.00; $Na_2HPO_4$, 1.15), the cells were counted and resuspended in 8 mL S-MEM (Gibco) ($Ca^{2+}$ free, with reduced $Mg^{2+}$ content) and stored at 4° C. until use.

For in-vitro tumor-cell accumulation studies, 5×10$^6$ cells in polypropylene test tubes were incubated at 37° C. or 4° C., with intermittent agitation with 1-2 µCi (5 µL) $^{99m}$Tc-complex Tc-(Compound A-D) in a total volume of 350 µL S-MEM. At appropriate time intervals the tubes were vortexed and 8-µL samples were layered on 350 µL cold FBS in a 400-µL Eppendorf microcentrifuge tube. After centrifugation at 15,000 rpm for 2 min, the tubes were frozen in a dry ice-acetone bath. While still frozen, the bottom tip of the microcentrifuge tube containing the cell pellet was cut and placed in a counting tube. The remaining portion of the tube with the supernatant was placed in a separate counting tube. Both fractions were counted for radioactivity in a γ-counter (WALLAC, 1480 WIZARD 3"™). The amount of supernatant in the cell pellet was determined to be <1% in separate experiments. The percentage cell uptake of the $^{99m}$Tc-complex was calculated as:

% uptake=[*cpm*(pellet)]/[*cpm*(pellet)+*cpm*(supernatant)]×100

The effect of the inhibitor DTG on cell uptake of these complexes was studied by addition of the inhibitor at various concentrations to the cell suspension 30 min prior to addition of the $^{99m}$Tc-complexes. Fresh DTG stock solutions were made by dissolving DTG (3.0 mg, 12.5 µmol) in 0.38 mL PBS and 0.12 mL hydrochloric acid (0.1 N) and subjecting the mixture to ultrasound until a clear solution was obtained, followed by the addition of 0.50 mL FBS to produce a neutral solution at pH 7.4. The stock solutions were diluted by an appropriate amount of S-MEM, and aliquots between 5 µL and 25 µL were added to the cell suspension such that the final concentration of DTG was between 0.02 µM and 120 µM in a total cell suspension volume of 350 µL.

Example 30

$\sigma_1$-Receptor Binding Assay. The in-vitro $\sigma_1$ binding affinities of complexes Re-(Compound A), Re-(Compound C), and Re-(Compound D) were determined in a competition assay using guinea pig brain membranes and the high-affinity $\sigma_1$-ligand [$^3$H]-(+)-pentazocine. The membranes were prepared from guinea pig brain (minus cerebellum) as previously described. Fifteen concentrations of the nonradioactive rhenium complexes ranging from 10$^{-10}$ to 10$^{-3}$ M and protein samples (0.15 mg membrane protein) were incubated with 5 nM [$^3$H]-(+)-pentazocine in a total volume of 0.25 mL Tris-HCl (50 mM), pH 8. Incubations were carried out for 120 min at 25° C. All assays were terminated by dilution with 5 mL ice-cold Tris-HCl (10 mM), pH 8.0, and the solutions were filtered through glass-fiber filters (Whatman GF/B; presoaked in 0.5% polyethyleneimine for 30 min at 25° C.). Filters were then washed twice with 5 mL ice-cold Tris-HCl (10 mM), pH 8.0, and counted in Hionic-Fluor cocktail (Packard, Groningen, The Netherlands). The corresponding $IC_{50}$ values were etermined using SigmaPlot software (SigmaPlot 4.0; SPSS Inc., Chicago, Ill.) and were used for the calculation of the apparent $K_i$ values using the Cheng-Prusoff equation (Cheng, Y.; Prusoff, W. H. Relationship between the Inhibition Constant $(K_I)$ and the Concentration of Inhibitor Which Causes 50 Per Cent Inhibition $(I_{50})$ of an Enzymatic Reaction. *Biochem. Pharmacol.* 1973, 22, 3099-3108.).

Example 31

$\sigma_2$-Receptor Binding Assay. Rat liver membranes were prepared from male Sprague-Dawley rat livers as previously described (Hellewell, S. B.; Bruce A.; Feinstein, G.; Orringer, J.; Williams, W.; Bowen, W. D. Rat Liver and Kidney Contain High Densities of $\sigma_1$ and $\sigma_2$ Receptors: Characterization by Ligand Binding and Photoaffinity Labeling. *Eur. J. Pharmacol.-Mol. Pharmacol. Sect.* 1994, 268, 9-18). The $\sigma_2$ receptors were labeled as described using [$^3$H]DTG as radioligand in the presence of 1 µM dextrallorphan to mask $\sigma_1$ receptors. Competition assays were performed with fifteen concentrations of the nonradioactive rhenium complexes ranging from $10^{-10}$ to $10^{-3}$ M and protein samples (0.15 mg membrane protein) in Tris-HCl (50 mM), pH 8.0, for 120 min at 25° C. in a 0.25-mL volume. All other manipulations and data analysis were performed as described vide supra for the $\sigma_1$ receptor assay.

Example 32

Animal Studies. All animal experiments were performed in compliance with the *Principles of Laboratory Animal Care* (NIH publication #85-23, revised 1985). Biodistribution studies and tumor-uptake measurements were performed in C57Bl6 mice (15 to 20 g) bearing the B16/F0 murine melanoma on the hind limb. See for example the studies described in, which are hereby incorporated by reference, Brandau, W.; Niehoff, T.; Pulawski, P.; Jonas, M.; Dutschka, K.; Sciuk, J.; Coenen, H. H.; Schober, O. Structure Distribution Relationship of Iodine-123-Iodobenzamides as Tracers for the Detection of Melanotic Melanoma. *J. Nucl. Med.* 1996, 37, 1865-1871; Mohanmmed, A.; Nicholl, C.; Titsch, U.; Eisenhut, M. Radiojodinated N-(Alkylaminoalkyl)-Substituted 4-Methoxy-, 4-Hydroxy-, and 4-Aminobenzamides: Biological Investigations for the Improvement of Melanoma-Imaging Agents. *Nucl. Med. Biol.* 1997, 24, 373-380; Titsch, U.; Mohammed, A.; Wagner, S.; Oberdorfer, F.; Eisenhut, M. Syntheses of N-(2-Diethylaminoethyl)benzamides Suitable for $^{99m}$Tc Complexation. *J. Labelled Compd. Radiopharm.* 1997, 40, 416-418; Dittmann, H.; Coenen, H. H.; Zölzer, F.; Dutschka, K.; Brandau, W.; Streffer, C. In Vitro Studies on the Cellular Uptake of Melanoma Imaging Aminoalkyl-iodobenzamide Derivatives (ABA). *Nucl. Med. Biol.* 1999, 26, 51-56; and Michelot, J. M.; Moreau, M. F. C.; Veyre, A. J.; Bonafous, J. F.; Bacin, F. J.; Madelmont, J. C.; Bussiere, F.; Souteyrand, P. A.; Mauclaire, L. P.; Chossat, F. M.; Papon, J. M.; Labarre, P. G.; Kauffmann, Ph.; Plagne, R. J. Phase II Scintigraphic Clinical Trial of Malignant Melanoma and Metastases with Iodine-123-N-(2-Diethylaminoethyl 4-Iodobenzamide). *J. Nucl. Med.* 1993, 34, 1260-1266. The tumor cells (B16/F0), obtained from ATCC, were washed with PBS and transplanted subcutaneously on the left hind flank by an inoculation of $0.5 \times 10^6$ cells (0.1 mL). Ten to 14 days later the animals developed palpable tumor nodules 3 to 5 mm in diameter. The biodistribution studies were carried out by tail-vein injection of 25 to 30 µCi (0.05 to 0.1 mL) of the $^{99m}$Tc-labeled complexes Tc-(Compound A-D, H, J, K or M). At the designated time after tail-vein administration, the animals were weighed and sacrificed. The organs and tumors were harvested and, when appropriate, blotted dry, weighed, and counted in a gamma counter along with technetium-99m standards of the injected dose. The results are expressed as % ID/g tissue (Table 4 and 5)

Integrating the radiometal within the pharmacophore of melanoma-targeting dialkylaminoethyl benzamides, such as IMBA, by replacing the aromatic ring with an oxometal-tetradentate ligand, e.g., an oxometal-DADT or oxometal-AADT moiety leads to metal complexes that display significant in-vivo melanoma accumulation. Similar to the earlier oxometal '3+1' complexes, these oxotechnetium(V)- and oxorhenium(V)-AADT complexes also contain pendant tertiary amines, and those possessing a log $D_{(pH\ 7.4)} \approx 1$ (complex Tc-Compound A) display relatively high in-vivo melanoma accumulation. While the σ-receptor affinity for all the complexes is low to moderate, in-vitro cell-uptake measurements indicate an active uptake component in B16 melanoma cells. The relatively high in-vivo melanoma uptake coupled with the high melanoma/nontumor ratios displayed by these technetium complexes indicates that technetium-based small molecular probes that target melanoma may be designed and could potentially be useful in the early detection and diagnosis of melanoma and its metastases.

The present invention has been described in detail. However, it will be appreciated that those skilled in the art may make modifications and improvements within the scope of the invention. For example, the pharmacore group may be linked to a carbon atom of the chelating ligand instead of to a nitrogen atom.

What is claimed is:
1. A compound represented by the formula:

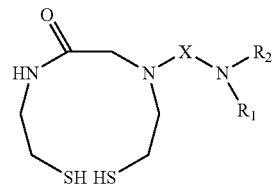

wherein:
$R_1$ and $R_2$ each are independently selected from lower alkyl group having 1 to about 4 carbon atoms; or
—$NR_1R_2$ taken in combination is a heterocyclic ring according to the formula:

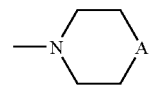

where A is $CH_2$, $NR_D$, O or S;
$R_D$ is chosen from the group consisting of hydrogen, lower alkyl group having from 1 to about 4 carbon atoms, aralkyl groups having from 7 to about 18 carbon atoms, aryl groups having 6 to about 18 carbon atoms, alkyl ester groups having about 2 to about 8 carbon atoms, and aryl ester groups having about 7 to about 18 carbon atoms;

X is a —$(CH_2)_q$ group; and q is an integer selected from 1 to 6.

2. The compound of claim 1, wherein the compound is capable of binding a metal ion selected from the group consisting of technetium, rhenium, yttrium, copper, gallium, indium, bismuth, platinum and rhodium.

3. The compound of claim 1, wherein the compound is capable of binding technetium or rhenium.

4. A compound represented by the formula:

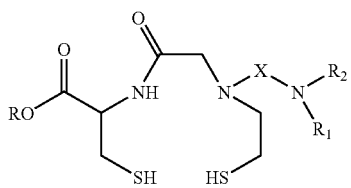

wherein:

R is a lower alkyl group having 1 to about 8 carbon atoms, or an alkoxyalkyl group having 2 to about 8 carbon atoms;

$R_1$ and $R_2$ each are independently selected from lower alkyl group having 1 to about 4 carbon atoms; or —$NR_1R_2$ taken in combination is a heterocyclic ring according to the formula:

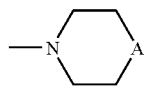

where A is $CH_2$, $NR_D$, O or S;

$R_D$ is chosen from the group consisting of hydrogen, lower alkyl group having from 1 to about 4 carbon atoms, aralkyl groups having from 7 to about 18 carbon atoms, aryl groups having 6 to about 18 carbon atoms, alkyl ester groups having about 2 to about 8 carbon atoms, and aryl ester groups having about 7 to about 18 carbon atoms;

X is a —$(CH_2)_q$ group; and q is an integer selected from 1 to 6.

5. A compound represented by the formula:

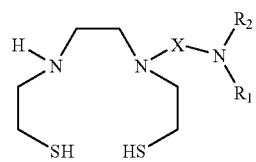

wherein:

$R_1$ and $R_2$ each are independently selected from lower alkyl group having 1 to about 4 carbon atoms; or —$NR_1R_2$ taken in combination is a heterocyclic ring according to the formula:

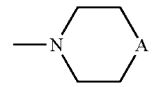

where A is $CH_2$, $NR_D$, O or S;

$R_D$ is chosen from the group consisting of hydrogen, lower alkyl group having from 1 to about 4 carbon atoms, aralkyl groups having from 7 to about 18 carbon atoms, aryl groups having 6 to about 18 carbon atoms, alkyl ester groups having about 2 to about 8 carbon atoms, and aryl ester groups having about 7 to about 18 carbon atoms;

X is a —$(CH_2)_q$ group; and q is an integer selected from 1 to 6.

6. A neutral or cationic radiolabeled complex comprising a metal ion and a compound that binds the metal ion, wherein the compound is a compound of claim 1.

7. The neutral or cationic radiolabeled complex of claim 6, wherein the metal ion is selected from the group consisting of technetium, rhenium, yttrium, copper, gallium, indium, bismuth, platinum and rhodium.

8. The neutral or cationic radiolabeled complex of claim 6, wherein the metal ion is technetium-99m or one or more isotopes of rhenium.

9. A neutral or cationic radiolabeled complex comprising a metal ion and a compound that binds the metal ion, wherein the compound a compound of claim 4.

10. A neutral or cationic radiolabeled complex comprising a metal ion and a compound that binds the metal ion, wherein the compound is a compound of claim 5.

11. A neutral or cationic radiolabeled complex of the formula:

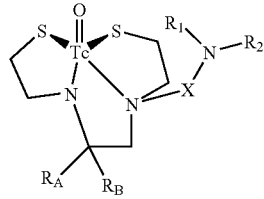

wherein $R_A$ and $R_B$ are each hydrogen or —$(CR_AR_B)$— taken in combination is —C=O—;

$R_1$ and $R_2$ each are independently selected from a lower alkyl group having 1 to about 4 carbon atoms; or —$NR_1R_2$ taken in combination is a heterocyclic ring according to the formula:

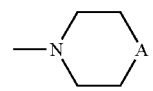

where A is $CH_2$, $NR_D$, O or S;

$R_D$ is chosen from the group consisting of hydrogen, lower alkyl group having from 1 to about 4 carbon atoms, aralkyl groups having from 7 to about 18 carbon atoms, aryl groups having 6 to about 18 carbon atoms, alkyl ester groups having about 2 to about 8 carbon atoms, and aryl ester groups having about 7 to about 18 carbon atoms;

X is a —(CH$_2$)$_q$ group; and q is 2, 3, or 4.

12. A neutral or cationic radiolabeled complex of the formula:

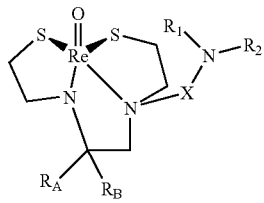

wherein

R$_A$ and R$_B$ are each hydrogen or —(CR$_A$R$_B$)— taken in combination is —C=O—;

R$_1$ and R$_2$ each are independently selected from a lower alkyl group having 1 to about 4 carbon atoms; or —NR$_1$R$_2$ taken in combination is a heterocyclic ring according to the formula:

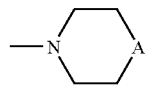

where A is CH$_2$, NR$_D$, O or S;

R$_D$ is chosen from the group consisting of hydrogen, lower alkyl group having from 1 to about 4 carbon atoms, aralkyl groups having from 7 to about 18 carbon atoms, aryl groups having 6 to about 18 carbon atoms, alkyl ester groups having about 2 to about 8 carbon atoms, and aryl ester groups having about 7 to about 18 carbon atoms;

X is a —(CH$_2$)$_q$ group; and q is 2,3, or 4.

13. A method for in-vivo or in-vitro imaging of at least one tumor comprising the steps of:
    (a) providing a radiolabeled neutral or cationic radiolabeled complex comprising a metal ion and a compound that binds the metal ion, wherein the compound is a compound according to claim 1.

14. The method of claim 13, wherein the metal ion is technetium-99m or one or more isotopes of rhenium.

15. The method of claim 13, wherein the tumor(s) are neoplasm(s).

16. The method of claim 13, wherein the tumor(s) are carcinoma(s).

17. The method of claim 13, wherein the tumor(s) are melanoma(s).

18. A method for the treatment of cancer comprising the steps of:
    (a) providing a cytotoxic metal complex comprising a metal ion and a compound that binds the metal ion, wherein the compound is a compound according to claim 1; and
    (b) contacting the tumor(s) with the cytotoxic metal complex.

19. A method of claim 18, wherein the metal ion is a radioactive isotope of technetium, rhenium, yttrium, copper, gallium, indium, bismuth, platinum, or rhodium.

* * * * *